(12) United States Patent
Kuhn et al.

(10) Patent No.: US 11,234,620 B2
(45) Date of Patent: Feb. 1, 2022

(54) PERFORMING MEASUREMENTS USING SENSORS OF A MEDICAL DEVICE SYSTEM

(71) Applicant: Medtronic, Inc., Minneapolis, MN (US)

(72) Inventors: Jonathan L. Kuhn, Ham Lake, MN (US); Can Cinbis, Salt Lake City, UT (US); Saul E. Greenhut, Aurora, CO (US)

(73) Assignee: Medtronic, Inc., Minneapolis, MN (US)

( * ) Notice: Subject to any disclaimer, the term of this patent is extended or adjusted under 35 U.S.C. 154(b) by 242 days.

(21) Appl. No.: 16/450,384

(22) Filed: Jun. 24, 2019

(65) Prior Publication Data

US 2020/0397355 A1 Dec. 24, 2020

(51) Int. Cl.
*A61B 5/1455* (2006.01)
*A61B 5/00* (2006.01)
(Continued)

(52) U.S. Cl.
CPC ........ *A61B 5/14552* (2013.01); *A61B 5/0031* (2013.01); *A61B 5/02154* (2013.01);
(Continued)

(58) Field of Classification Search
CPC .............. A61B 5/14552; A61B 5/0031; A61B 5/02154; A61B 5/118; A61B 5/1459;
(Continued)

(56) References Cited

U.S. PATENT DOCUMENTS

| | | |
|---|---|---|
| 5,025,791 A | 6/1991 | Niwa |
| 5,368,224 A | 11/1994 | Richardson et al. |

(Continued)

FOREIGN PATENT DOCUMENTS

| | | |
|---|---|---|
| CN | 109222994 | 1/2019 |
| EP | 897692 A2 | 2/1999 |

OTHER PUBLICATIONS

PCT/US2020/033097, The International Search Report and Written Opinion, dated Jul. 20, 2020, 8pages.
(Continued)

*Primary Examiner* — Eric F Winakur
*Assistant Examiner* — Abid A Mustansir
(74) *Attorney, Agent, or Firm* — Shumaker & Sieffert, P.A.

(57) ABSTRACT

This disclosure is related to devices, systems, and techniques for performing patient parameter measurements. In some examples, a medical device system includes an optical sensor configured to measure ambient light and a tissue oxygen saturation parameter and processing circuitry configured to determine that a current measurement of the tissue oxygen saturation parameter is prompted and control the optical sensor to perform an ambient light measurement associated with the current measurement of the tissue oxygen saturation parameter. The processing circuitry is further configured to determine, based on the ambient light measurement, at least one of whether to control the optical sensor to perform the current measurement of the tissue oxygen saturation parameter, when to control the optical sensor to perform the current measurement of the tissue oxygen saturation parameter, or whether to include the current measurement of the tissue oxygen saturation parameter in a trend of the tissue oxygen saturation parameter.

20 Claims, 12 Drawing Sheets

(51) Int. Cl.
*A61B 5/0215* (2006.01)
*A61B 5/11* (2006.01)
*A61B 5/1459* (2006.01)

(52) U.S. Cl.
CPC .......... *A61B 5/1118* (2013.01); *A61B 5/1459* (2013.01); *A61B 5/686* (2013.01); *A61B 5/1123* (2013.01); *A61B 5/6826* (2013.01); *A61B 5/7207* (2013.01); *A61B 5/7221* (2013.01); *A61B 2560/0209* (2013.01); *A61B 2562/0219* (2013.01)

(58) Field of Classification Search
CPC ..... A61B 5/686; A61B 5/1123; A61B 5/6826; A61B 5/7207; A61B 5/7221; A61B 2560/029; A61B 2562/0219
See application file for complete search history.

(56) References Cited

U.S. PATENT DOCUMENTS

| | | | |
|---|---|---|---|
| 6,198,952 | B1 | 3/2001 | Miesel |
| 6,409,675 | B1 | 6/2002 | Turcott |
| 6,480,733 | B1 | 11/2002 | Turcott |
| 7,991,448 | B2 | 8/2011 | Edgar, Jr. et al. |
| 9,788,793 | B2 | 10/2017 | Zong et al. |
| 2008/0208020 | A1 | 8/2008 | Cinbis et al. |
| 2009/0326350 | A1* | 12/2009 | Kracker ............ A61B 5/14542 600/324 |
| 2010/0106220 | A1 | 4/2010 | Ecker et al. |
| 2010/0185262 | A1* | 7/2010 | Kuhn ............... A61B 5/1495 607/60 |
| 2010/0317942 | A1 | 12/2010 | Cinbis et al. |
| 2010/0318149 | A1 | 12/2010 | Kuhn et al. |
| 2011/0066206 | A1* | 3/2011 | Kuhn ............... A61N 1/36557 607/22 |
| 2012/0123226 | A1 | 5/2012 | Schwenk et al. |
| 2013/0289372 | A1 | 10/2013 | Imran |
| 2016/0081601 | A1 | 3/2016 | Ballam et al. |
| 2016/0374597 | A1* | 12/2016 | Stahmann ......... A61B 5/14532 600/309 |
| 2018/0279924 | A1 | 10/2018 | Kuhn |

OTHER PUBLICATIONS

Myers et al., "Noninvasive method for measuring local hemoglobin oxygen saturation in tissue using wide gap second derivative near-infared spectroscopy," Journal of Biomedical Optics, May/Jun. 2005, 18 pp.
Podbregar et al., "Skeletal muscle oxygen saturalion does not estimate mixed venous oxygen saturation in patients with severe left heart failure and additional severe sepsis or septic shock," Critical Care, vol. 11, No. 1, Jan. 16, 2007, 8 pp.
Myers et al., "Tissue hemoglobin index: a non-invasive optical measure of total tissue hemoglobin," Critical Care, vol. 3, Suppl 5, Nov. 30, 2009, 13 pp.
Desai et al., "Rehospitalization for Heart Failure—Predict or Prevent?," American Heart Association Journals, Jul. 24, 2012, 6 pp.
Fontaine et al., "Reflectance-Based Pulse Oximeter for the Chest and Wrist," Worcester Polytechnic Institute, Apr. 2013, 131 pp.
Charach et al., "Internal Thoracic Impedance—A Useful Method for Expedient Detection and Convenient Monitoring of Pleural Effusion," PLoS One, Apr. 28, 2015, 14 pp.
Dunlay et al., "Hospitalizations After Heart Failure Diagnosis: A Community Perspective," Journal of the American College of Cardiology, vol. 54, Issue 18, Oct. 27, 2009, 16 pp.
Blecker et al., "Heart Failure Associated Hospitalizations in the United States," Journal of the American College of Cardiology, vol. 61, Issue 12, Mar. 26, 2013, 17 pp.
Blecker et al., "Quality of Care for Heart Failure Patients Hospitalized for Any Cause," Journal of the American College of Cardiology, vol. 63, Issue 2, Jan. 21, 2014, 15 pp.
Pollard et al., Validation in Volunteers of a Near-Infared Spectroscope for Monitoring Brain Oxygenation In Vivo., Anesthesia & Analgesia, vol. 82, Mar. 1996, 9 pp.
Hogan et al., "The Utility of Microvascular Perfusion Assessment in Heart Failure: A Pilot Study," Journal of Cardiac Failure, vol. 11, Issue 9, Jul. 14, 2005, 8 pp.
Hogan et al., "Quantitative tissue hemoglobin oxygen saturation measurement in decompensated heart failure," Journal of Cardiothoracic-Renal Research, vol. 1, May 18, 2006, 6 pp.
Hogan et al., "Peripheral tissue oxygenation improves during ED treatment of acute heart failure," American Journal of Emergency Medicine, vol. 30, Oct. 19, 2010, 8 pp.

* cited by examiner

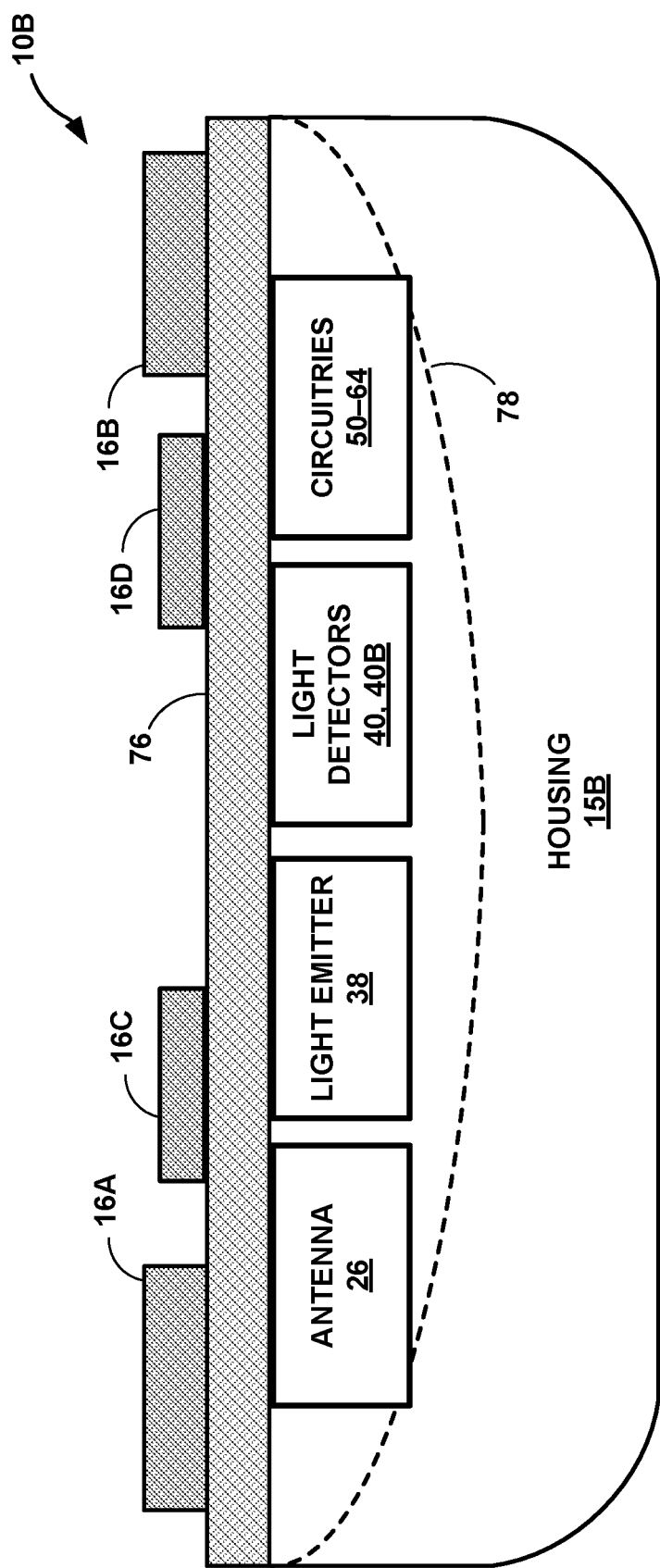

PERFORMING MEASUREMENTS USING SENSORS OF A MEDICAL DEVICE SYSTEM

TECHNICAL FIELD

The disclosure relates generally to medical device systems and, more particularly, medical device systems configured to sense one or more parameters.

BACKGROUND

Some types of medical devices may be used to monitor one or more physiological parameters of a patient. Such medical devices may include, or may be part of a system that includes, sensors that detect signals associated with such physiological parameters. Values determined based on such signals may be used to assist in detecting changes in patient conditions, in evaluating the efficacy of a therapy, or in general evaluating patient health. For example, medical devices that monitor physiological parameters may analyze values associated with such physiological parameters in order to identify or monitor a patient condition.

SUMMARY

In general, the disclosure is directed to devices, systems, and techniques for performing measurements of at least one patient parameter to determine or monitor one or more patient conditions. For example, this disclosure describes techniques for performing any combination of tissue oxygen saturation ($StO_2$) measurements, pulse oximetry ($SpO_2$) measurements, or other parameter measurements to determine whether the patient is experiencing or will soon experience an exacerbation in a patient condition such as heart failure, sleep apnea, or chronic obstructive pulmonary disease (COPD). In some examples, this disclosure describes techniques for performing parameter measurements to track a patient condition as the patient condition is returning to a stable state after the patient condition is exacerbated. In addition to measuring oxygen saturation levels, the medical device may, in some examples, use various sensors and electrodes to measure one or more of a patient motion level, patient posture, electrocardiogram (ECG) signals, tissue impedance signals, doppler flow signals, an amount of ambient light present in target tissue, a quality of an optical sensor test signal, a temperature of the target tissue, a respiration rate, a heart rate, and a heart rate variability. Such measurements performed by the medical device may produce data that processing circuitry may analyze to assess the one or more patient conditions. Data obtained by the medical device corresponding to such parameter measurements may be analyzed by processing circuitry to determine whether the medical device performs or retains certain parameter measurements, such as oxygen saturation measurements.

In some examples, this disclosure describes techniques for using a medical device to perform a set of evaluations, where each evaluation of the set of evaluations represents a decision of whether to perform a parameter measurement using the medical device, or whether to classify a parameter measurement as being high-quality or low-quality. In some cases, the medical device is powered by a power source (e.g., a battery) with a limited capacity. In some cases, the medical device is powered by a power source (e.g., an energy harvester), with a self-replenishing capacity. Each parameter measurement performed by the medical device may drain an amount of energy (e.g., electrical current) from the power source. In some examples, it may be beneficial to preserve the capacity of the power source by limiting an amount of energy drained from the power source by components of the medical device. Consequently, it may be helpful to determine, before performing a parameter measurement, if the parameter measurement will produce high-quality data. In some cases, the medical device may draw energy from the power source to perform a parameter measurement only when the parameter measurement produces data that is useful for determining a patient condition such as heart failure, sleep apnea, or COPD. In some cases, data from parameter measurements may be sorted into a high-quality group and a low-quality group, where the high-quality data is analyzed to identify or monitor patient conditions—while excluding the low-quality data. In such cases, a quality of the analysis may be improved by excluding the low-quality data.

An example parameter measurement may include an $StO_2$ measurement. $StO_2$ may be a weighted average of arterial blood oxygen saturation ($SaO_2$) and venous blood oxygen saturation ($SvO_2$), where $SvO_2$ is more heavily weighted than $SaO_2$. If $StO_2$ remains stable over a period of time, this may indicate that $SaO_2$ is also stable. However, if $StO_2$ falls, the processing circuitry may, in some cases output an instruction to measure $SaO_2$ in order to determine whether the fall in $StO_2$ corresponds to a fall in $SaO_2$, and to determine if the fall in $SaO_2$ exceeds clinically accepted thresholds indicating an important change in patient status. In some examples, to obtain data indicative of $SaO_2$, the processing circuitry may output an instruction to the medical device to perform an $SpO_2$ measurement. In other examples, to obtain data indicative of $SaO_2$, the processing circuitry may output an instruction to an external pulse oximetry device to perform the $SpO_2$ measurement. $SpO_2$ measurements performed by the medical device may consume significantly more energy than $StO_2$ measurements. As such, it may be beneficial to instruct the medical device to perform $SpO_2$ measurements when determined necessary to confirm and interpret an $StO_2$ trend.

The techniques of this disclosure may provide one or more advantages. For example, the medical device may be configured to perform the set of determinations to ascertain whether parameter measurements will produce data reliable for tracking patient conditions. In some examples, for each evaluation of the set of evaluations, the medical device measures an amount of ambient light present in target tissue, and the medical device measures a patient motion level based on accelerometer signals. If the amount of ambient light and the patient motion level are below a threshold amount of ambient and a threshold motion level, respectively, processing circuitry may instruct the medical device to perform a parameter measurement and/or may determine that the parameter measurement should be retained for further processing. Consequently, in some cases, by monitoring ambient light and patient motion, the processing circuitry may prevent the medical device from performing the parameter measurement if the amount of ambient light or the patient motion level is high enough to compromise the parameter measurement, thus preventing the medical device from drawing energy from the power source to perform a measurement that will produce inadequate data, and/or may improve the quality of the data used to track a patient condition. Additionally, the processing circuitry may decrease an amount of energy consumed by the medical device by limiting a number of $SpO_2$ measurements performed by the medical device based on a stability of the $StO_2$ measurements. In some examples, this approach may ensure that the medical device waits for periods of low light and motion to take reliable measurements.

In some examples, a medical device system includes an optical sensor configured to measure ambient light and a tissue oxygen saturation parameter. Additionally, the medical device system includes processing circuitry configured to determine that a current measurement of the tissue oxygen saturation parameter is prompted and control the optical sensor to perform an ambient light measurement associated with the current measurement of the tissue oxygen saturation parameter. The processing circuitry is further configured to determine, based on the ambient light measurement, at least one of whether to control the optical sensor to perform the current measurement of the tissue oxygen saturation parameter, when to control the optical sensor to perform the current measurement of the tissue oxygen saturation parameter, or whether to include the current measurement of the tissue oxygen saturation parameter in a trend of the tissue oxygen saturation parameter.

In some examples, a method includes measuring, using an optical sensor of a medical device system, ambient light and a tissue oxygen saturation parameter, determining, using processing circuitry of the medical device system, that a current measurement of the tissue oxygen saturation parameter is prompted, and controlling the optical sensor to perform an ambient light measurement associated with the current measurement of the tissue oxygen saturation parameter. Based on the ambient light measurement, the method further includes performing at least one of: determining whether to control the optical sensor to perform the current measurement of the tissue oxygen saturation parameter, determining when to control the optical sensor to perform the current measurement of the tissue oxygen saturation parameter, or determining whether to include the current measurement of the tissue oxygen saturation parameter in a trend of the tissue oxygen saturation parameter.

In some examples, a non-transitory computer-readable medium stores instructions for causing processing circuitry to perform a method including using an optical sensor of a medical device system, ambient light and a tissue oxygen saturation parameter, determining, using processing circuitry of the medical device system, that a current measurement of the tissue oxygen saturation parameter is prompted, and controlling the optical sensor to perform an ambient light measurement associated with the current measurement of the tissue oxygen saturation parameter. Based on the ambient light measurement, the method further includes performing at least one of: determining whether to control the optical sensor to perform the current measurement of the tissue oxygen saturation parameter, determining when to control the optical sensor to perform the current measurement of the tissue oxygen saturation parameter, or determining whether to include the current measurement of the tissue oxygen saturation parameter in a trend of the tissue oxygen saturation parameter.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

FIGS. 4A and 4B are block diagrams illustrating two additional example IMDs that may be substantially similar to the IMD of FIGS. 1-3, but which may include one or more additional features, in accordance with one or more techniques described herein.

Like reference characters denote like elements throughout the description and figures.

DETAILED DESCRIPTION

Figure 1:
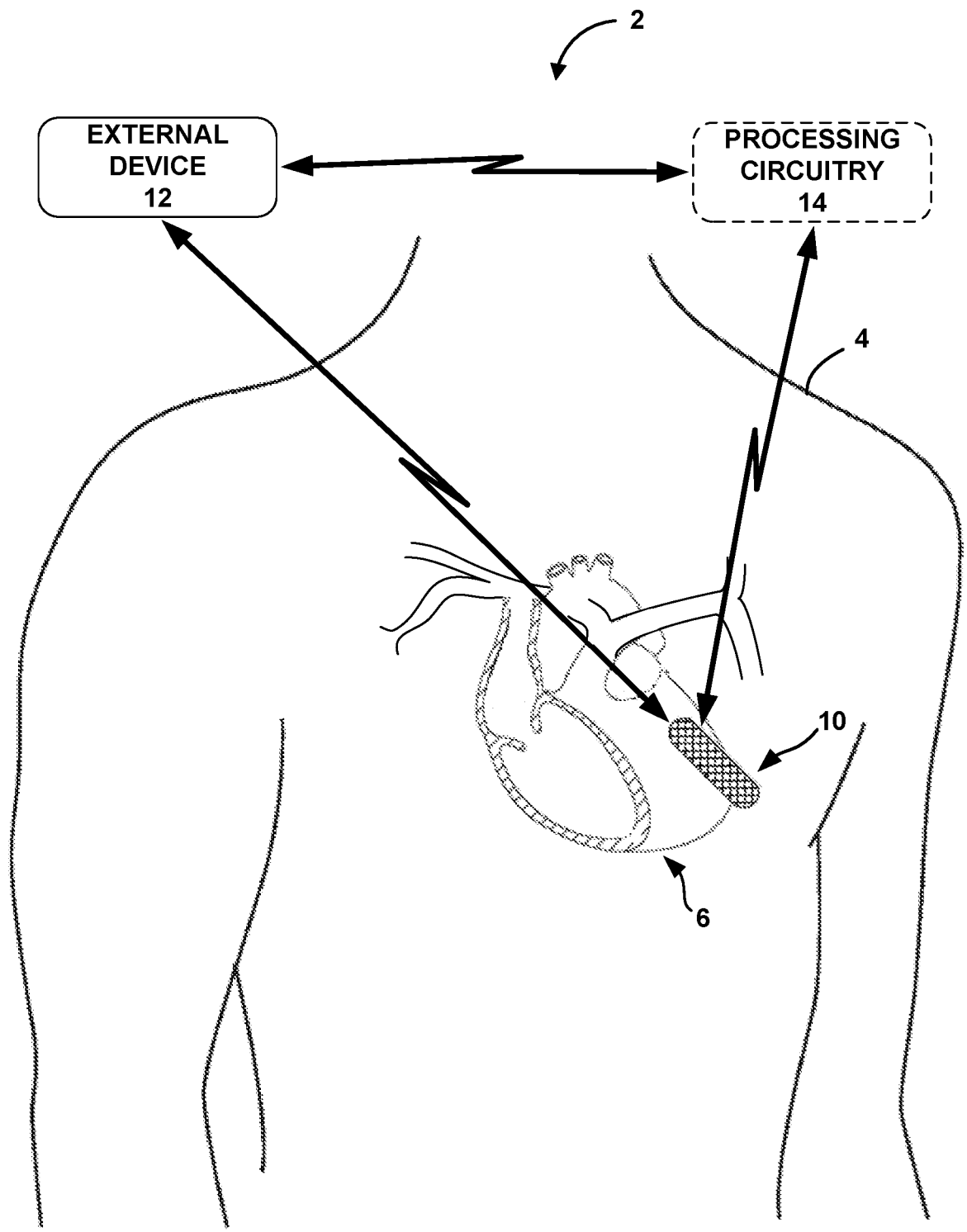
FIG. 1 is a conceptual drawing illustrating an example of a medical device system in conjunction with a patient, in accordance with one or more techniques described herein.

This disclosure describes techniques for performing patient parameter measurements. For example, processing circuitry may perform an evaluation to determine whether the processing circuitry instructs a device to perform a primary parameter measurement associated with a patient. To perform the evaluation, the processing circuitry may output an instruction to an implantable medical device (IMD), the instruction causing the IMD to perform a set of secondary parameter measurements. Based on data associated with the set of secondary parameter measurements, the processing circuitry may determine whether to instruct the IMD to perform the primary measurement. In some cases, the set of secondary parameter measurements may consume a smaller amount of energy than the primary parameter measurement. Additionally, in some cases, the data associated with the set of secondary parameter measurements may indicate whether a primary parameter measurement will produce high-quality data for identifying or monitoring a patient condition such as heart failure, sleep apnea, or chronic obstructive pulmonary disease (COPD). In this way, by instructing the IMD to perform the set of secondary parameter measurements, the processing circuitry may prevent the IMD from spending energy to obtain inadequate data or identify data points that may be disregarded during analysis. The techniques of this disclosure are not limited to implantable devices or medical devices. The techniques may be used to perform an evaluation to determine whether to instruct any device or combination of devices to perform parameter measurements. As used herein, the adjectives "primary" and "secondary" are not intended to indicate an order or a preference between groups, but rather are used merely to distinguish between groups.

In some examples, the primary parameter measurement includes a tissue oxygen saturation ($StO_2$) measurement. $StO_2$ may, in some examples, represent a weighted average between Arterial blood oxygen saturation ($SaO_2$) and venous oxygen saturation ($SvO_2$). In some examples, the primary parameter measurement includes a pulse oximetry ($SpO_2$) measurement. $SpO_2$ may, in some cases, represent an approximation of $SaO_2$. Oxygen saturation (e.g., $StO_2$, $SaO_2$, $SvO_2$, and $SpO_2$) trends may be indicative of one or more patient conditions, such as heart failure, sleep apnea, or COPD, as examples. For example, a steady decline of $StO_2$ values over a period time may indicate a worsening risk of a heart failure exacerbation in a patient. As such, the IMD may perform several $StO_2$ measurements over a period of time (e.g., hours, days, weeks, or months) and the processing circuitry may identify a trend of $StO_2$ values using data from the $StO_2$ measurements. Based on the identified trend, the processing circuitry may, in some cases, identify a medical condition present in the patient or monitor a condition that is already known to be present in the patient.

In order to perform an $StO_2$ measurement, the IMD may employ an optical sensor. The optical sensor may, in some cases, include two or more light emitters and one or more light detectors. During the respective $StO_2$ measurement, the light emitters may output light to an area of tissue proximate to the IMD, the light including a first set of frequency components. The one or more light detectors may sense light including a second set of frequency components. The processing circuitry is configured to compare the first set of frequency components and the second set of frequency components to identify an $StO_2$ value corresponding to the respective $StO_2$ measurement, where the $StO_2$ value represents a ratio of oxygen-saturated hemoglobin located in the area of tissue to a total amount of hemoglobin located in the area of tissue.

The light emitters of the optical sensor may, in some cases, consume significantly more energy than the one or more light detectors of the optical sensor. Additionally, the IMD may be powered by a power source (e.g., a battery) that is equipped with a limited amount of charge. For these reasons, among other reasons, it may be beneficial to limit an amount of time that the light emitters are activated, thus limiting a number of $StO_2$ measurements performed by the IMD. As discussed above, techniques of this disclosure may enable the processing circuitry to determine whether an $StO_2$ measurement performed at a particular time will produce a high-quality $StO_2$ value (e.g., low levels of noise present in the $StO_2$ value). In other words, the processing circuitry may be configured to direct the IMD to perform the set of secondary parameter measurements, where the set of secondary parameter measurements produce a set of secondary parameter values that the processing circuitry may use to perform an evaluation to determine whether to instruct the IMD to perform the primary parameter measurement (e.g., the $StO_2$ measurement).

In some examples, the set of secondary parameter measurements includes a motion level measurement and an ambient light measurement. To perform the motion level measurement, the IMD may use a motion sensor, for example an accelerometer, to sense data indicative of a motion level of the patient. For example, the motion sensor may measure an acceleration value of the IMD for a period of time. In some examples, the acceleration value includes three acceleration components (e.g., x-axis acceleration, y-axis acceleration, and z-axis acceleration). A relatively high amount of acceleration may indicate that the patient is engaging in a physical activity such as jogging, walking, or playing a sport—or engaging in another form of motion. In some cases, motion may introduce noise into a measurement (e.g., an $StO_2$ measurement) performed using the optical sensor, thus making the measurement unreliable. As such, the processing circuitry may compare the motion level corresponding to the motion level measurement with a threshold motion level. The processing circuitry may determine not to output an instruction directing the IMD to perform an $StO_2$ measurement if the motion level is greater than or equal to the threshold motion level.

In order to perform the ambient light measurement, the IMD may use the optical sensor, and more specifically, the one or more light detectors of the optical sensor, to obtain data indicative of an amount of ambient light present in an area of tissue proximate to the IMD. Since $StO_2$ measurements may include emitting light using the light emitters of the optical sensor and sensing light using the one or more light detectors, ambient light may introduce noise into the light sensed by the one or more light detectors, and consequently introduce noise into an $StO_2$ value determined from an $StO_2$ measurement. For example, ambient light may "confound" $StO_2$ data by making a particular $StO_2$ measurement appear as though oxygen levels are changing in the patient, even though the apparent changes are due to ambient light and not due to an exacerbation of a patient condition. Additionally, in some examples, ambient light "saturates" the light detectors of the optical sensor, causing an electrical output of the optical sensor to reach a maximum electric output level, rendering the light sensors incapable of providing data required for accurately measuring $StO_2$ levels. Consequently, it may be beneficial to avoid performing $StO_2$ measurements while high amounts of ambient light are present in the area of tissue surrounding the IMD, or exclude from analysis $StO_2$ measurements performed at times in which high amounts of ambient light are present. As such, the processing circuitry may compare the amount of ambient light corresponding to the ambient light measurement with a first threshold amount of ambient light. The processing circuitry may determine not to output an instruction directing the IMD to perform an $StO_2$ measurement if the amount of ambient light is greater than or equal to the first threshold amount of ambient light. Additionally, in some examples, if the amount of ambient light is greater than or equal to a second threshold amount of ambient light and less than the first threshold amount of ambient light, then the processing circuitry or IMD may subtract the ambient light from data corresponding to the $StO_2$ measurement.

In some examples, the set of secondary parameter measurements includes a posture measurement. Based on the signals provided by the motion sensor, the IMD may determine a posture (e.g., sitting standing, or lying down) of the patient. The IMD may determine whether to perform an $StO_2$ measurement or determine to include an $StO_2$ measurement in an analysis of $StO_2$ data based on the determined posture, e.g., such that the $StO_2$ measurements are preferentially taken, or not taken, when the patient is within one or more postures.

If the motion level is less than the threshold motion level and the amount of ambient light is less than the threshold amount of ambient light, the processing circuitry may output an instruction directing the IMD to perform an $StO_2$ measurement. Subsequently, the IMD may perform the $StO_2$ measurement to obtain data indicative of an $StO_2$ value and output the data to the processing circuitry. Based on the $StO_2$ value and, in some examples, other $StO_2$ values associated with previous $StO_2$ measurements, the processing circuitry may identify a trend of $StO_2$ values. The processing circuitry may compare the trend of $StO_2$ values with one or more sample trends of $StO_2$ values to determine if the patient is experiencing a particular patient condition or to monitor a patient condition to determine if the patient condition is worsening or exacerbating. For example, a decrease of $StO_2$ values over a period of time may indicate that a patient condition is worsening or exacerbating. However, since $StO_2$ may be a weighted average of $SaO_2$, and $SvO_2$, it may be beneficial to perform an $SpO_2$ measurement to confirm that a cause of the trend of $StO_2$ values is related more closely to an $SaO_2$ trend than an $SvO_2$ trend. Likewise, if $StO_2$ is not changing, then it may be unlikely that $SpO_2$ is changing, and therefore it may not be necessary to complete an $SpO_2$ measurement. As such, based on the comparison of the trend of $StO_2$ values with the one or more sample trends of $StO_2$ values, the processing circuitry may output an instruction directing a device to perform an $SpO_2$ measurement to obtain an $SpO_2$ value. In some examples, the device is the IMD. In other examples, the device is a device other than the IMD that is configured for performing $SpO_2$ measurements. If the $SpO_2$ value confirms that the trend of $StO_2$ values is indeed indicative of a worsening of the patient condition, the processing circuitry may output an alert.

In some examples, processing circuitry may analyze, based on any combination of a set of parameters, a set of $StO_2$ values each corresponding to a respective $StO_2$ measurement. For example, if the IMD performs an $StO_2$ parameter measurement, the IMD may also perform measurements of the set of other parameters to obtain a set of parameter values. In this way, the set of parameter values may be associated with the respective $StO_2$ measurement. In some examples, the set of parameters includes an amount of ambient light present in target tissue, an optical sensor test signal, a temperature of the target tissue, a posture of the patient, a respiration rate, a respiration volume, a heart rate, a heart rate variability, a tissue hemoglobin index (THI), and/or a subcutaneous tissue impedance. To analyze the set of $StO_2$ values associated with different postures, as an example, the processing circuitry may, in some cases, use the measured posture parameter values to identify a first subset of $StO_2$ values that correspond to $StO_2$ parameter measurements performed by the IMD while the patient lies in a prone position and identify a second subset of $StO_2$ values that correspond to $StO_2$ parameter measurements performed by the IMD while the patient lies in a supine position. Put another way, the processing circuitry, in some cases, may classify $StO_2$ values based on one or more conditions corresponding to the respective $StO_2$ measurements are taken, the one or more conditions being given by the sets of parameter values that are measured at each $StO_2$ measurement.

In this manner, the processing circuitry analyze together sets of $StO_2$ values that were measured at different times but under similar measurement conditions with regard to the other parameters. Trends in such grouped $StO_2$ values over time may indicate changes to a condition of the patient due to factors unrelated to the changes in the values of the other parameters. Comparison between $StO_2$ values from different groups may indicate a degree of sensitivity of $StO_2$ values to changes in the other parameters, e.g., how $StO_2$ values change with posture, which may also indicate one or more conditions of the patient.

FIG. 1 illustrates the environment of an example medical device system 2 in conjunction with a patient 4, in accordance with one or more techniques of this disclosure. The example techniques may be used with an IMD 10, which may be in communication with an external device 12 and processing circuitry 14. In some examples, IMD 10 is implanted outside of a thoracic cavity of patient 4 (e.g., subcutaneously in the pectoral location illustrated in FIG. 1). IMD 10 may be positioned near the sternum near or just below the level of heart 6, e.g., at least partially within the cardiac silhouette. In some examples, IMD 10 takes the form of a LINQ™ Insertable Cardiac Monitor (ICM), available from Medtronic plc, of Dublin, Ireland. External device 12 may be a computing device configured for use in settings such as a home, clinic, or hospital, and may further be configured to communicate with IMD 10 via wireless telemetry. For example, external device 12 may be coupled to a remote patient monitoring system, such as Carelink®, available from Medtronic plc, of Dublin, Ireland. External device 12 may, in some examples, include a programmer, an external monitor, or a consumer device such as a smart phone or tablet. Processing circuitry 14 may, in some examples, represent processing circuitry located within any combination of IMD 10 and external device 12. Additionally, in some examples, processing circuitry 14 may include processing circuitry located within another device or group of devices that are not illustrated in FIG. 1.

IMD 10 may include a plurality of electrodes (not illustrated in FIG. 1) and a set of sensors including one or more optical sensors (not illustrated in FIG. 1), which collectively detect signals that enable processing circuitry 14 to determine current values of at least one patient parameter associated with patient 4, and evaluate patient 4 for medical conditions (e.g., heart failure, sleep apnea, or chronic obstructive pulmonary disease (COPD)) based on such values. The at least one parameter may include, as examples, any combination of $StO_2$, $rSO_2$, $SpO_2$, $SvO_2$, $SaO_2$, patient motion level, patient posture, ambient light level, optical signal quality, subcutaneous tissue impedance, heart rate, heart rate variability, respiration rate, respiration volume, pulse transit time, temperature, and THI.

The one or more optical sensors may include at least two light emitters and at least one light detector. In some examples, IMD 10 may perform $StO_2$ measurements by emitting light via the light emitters and detecting light via the at least one light detector. To determine an $StO_2$ value, processing circuitry 14 may, in some examples, compare a frequency spectrum of light emitted from the at least two emitters and a frequency spectrum of light received by the at least one light detector. $StO_2$ may represent a weighted average of $SaO_2$ and $SvO_2$. In some examples, an $StO_2$ value may be equal to the sum of one quarter of an $SaO_2$ value and three quarters of an $SvO_2$ value. Additionally, in some examples, an $StO_2$ value may be equal to the sum of one third of an $SaO_2$ value and two thirds of an $SvO_2$ value.

In some examples, to monitor a patient condition such as heart failure, sleep apnea, or COPD, IMD 10 performs a set of $StO_2$ measurements using the one or more optical sensors. IMD 10 may output data indicative of the set of $StO_2$ measurements to processing circuitry 14. Based on the data indicative of the set of $StO_2$ measurements, the processing circuitry 14 may determine a $StO_2$ value corresponding to each $StO_2$ value of the set of $StO_2$ values. Additionally, in some examples, processing circuitry 14 may determine a trend of $StO_2$ values. In some cases, if the trend indicates that the $StO_2$ values are decreasing over a period of time (e.g., the trend is not stable), processing circuitry 14 may determine that a patient condition is worsening. In some such cases, processing circuitry 14 may output an alert recommending a course of action for patient 4.

Certain factors may, in some cases, introduce noise into $StO_2$ data produced from $StO_2$ measurements, or otherwise decrease a quality of the $StO_2$ data. Such factors may include a level of ambient light present in an area of tissue near IMD 10 or a motion level of patient 4 at the time in which an $StO_2$ measurement is made by IMD 10. Generally, low amounts of ambient light and low levels of patient motion are conducive to a high quality $StO_2$ measurement. As such, IMD 10 may measure an amount of ambient light present in tissue surrounding IMD 10 and measure a level of motion in patient 4 prior to performing an $StO_2$ measurement.

For example, processing circuitry 14 may be configured to determine, based on a motion level associated with patient 4 and based on an amount of ambient light present in tissue of patient 4 surrounding IMD 10, whether to output an instruction directing IMD 10 to perform an $StO_2$ measurement using an optical sensor. To determine whether to output the instruction to IMD 10, processing circuitry 14 may output an instruction directing IMD 10 to perform a motion level measurement using a motion sensor (not illustrated in FIG. 1). In some cases, the motion sensor is an accelerometer. The accelerometer may be configured to determine an acceleration value of IMD 10 over a period of time, the acceleration value including acceleration components in any of three dimensions (e.g., x-axis, y-axis, and z-axis). IMD 10 may output data indicative of the motion level measurement to processing circuitry 14. The acceleration of IMD 10, as measured by the at least one motion sensor of IMD 10, may be indicative of the motion level of patient 4. For example, if patient 4 is walking, running, playing a sport, or moving in another way, data from the one or more motion sensors may indicate greater acceleration values, and thus a greater level of patient motion, than if patient 4 is sitting or lying motionless. Additionally, data from the at least one motion sensor may indicate a posture such as sitting, standing, or lying down (e.g., supine, prone, lying on the left side, and lying on the right side) of patient 4. In some examples, Patient motion may skew $StO_2$ measurements such that $StO_2$ measurements performed by IMD 10 while patient 4 is more mobile may be less valuable for evaluating a patient condition than $StO_2$ measurements performed by IMD 10 while patient 4 is less mobile.

Additionally, processing circuitry 14 may output an instruction directing the medical device to perform an ambient light measurement using the optical sensor. IMD 10 may activate light emitters of the optical sensor to perform an $StO_2$ measurement or an $SpO_2$ measurement. However, in some examples, to perform an ambient light measurement, it may be sufficient for IMD 10 to activate at least one light detector of the optical sensor—without activating the light emitters. In this way, performing an ambient light measurement may consume a smaller amount of energy than performing an $StO_2$ measurement. IMD 10 may, in some cases, output data corresponding to the ambient light measurement to processing circuitry 14 for analysis.

After receiving the data corresponding to the motion level, processing circuitry 14 may be configured to determine a motion level associated with patient 4. Processing circuitry 14 may determine the motion level based on acceleration data, where greater acceleration values are indicative of a greater level of patient motion. Additionally, after receiving the data corresponding to the ambient light measurement, processing circuitry 14 may be configured to determine an amount of ambient light present in a portion of the tissue surrounding IMD 10. Ambient light may be detected by light detectors of IMD 10. However, IMD 10 might not, in some cases, need to activate the light emitters in order to detect ambient light. As such, an ambient light measurement may consume a smaller amount of energy than an $StO_2$ measurement or an $SpO_2$ measurement—both of which employ the light emitters for different periods of time. Processing circuitry 14 may compare the motion level with a threshold motion level and compare the amount of ambient light with a threshold amount of ambient light. The threshold motion level and the threshold amount of ambient light may be stored in a storage device of IMD 10, external device 12, another storage device in communication with processing circuitry 14, or any combination thereof.

In some cases, if the motion level is lower than the threshold motion level and the amount of ambient light is lower than the threshold amount of ambient light, processing circuitry 14 may output an instruction to IMD 10 to perform an optical test measurement. Subsequently, IMD 10 may perform the optical test measurement to obtain an optical test signal. IMD 10 may output the optical test signal to processing circuitry 14 for analysis. In some examples, the optical test measurement includes an activation of the optical sensor (e.g., light emitters and light detectors) of IMD 10. In some examples, the optical test signal resulting from the optical test measurement may include a sequence of datapoints, the sequence having a duration between one second and ten seconds. The sequence may include a set of frequency components ranging between 4 Hertz (Hz) and 55 Hz. Processing circuitry 14 may be configured to determine whether the optical test signal quality is adequate. For example, processing circuitry 14 may analyze the set of frequency components of the optical test signal to determine whether the optical sensor of IMD 10 is presently capable of generating high-quality optical data.

In some examples, processing circuitry 14 is configured to determine to output the instruction directing IMD 10 to perform an $StO_2$ measurement if the motion level is greater than or equal to the threshold motion level, if the amount of ambient light is greater than or equal to the threshold amount of ambient light, or if processing circuitry 14 determines that the optical test signal is not adequate. However, in such examples, processing circuitry is configured to indicate that the $StO_2$ measurement is being performed under adverse conditions that may potentially compromise data collected during the $StO_2$ measurement. Subsequently, IMD 10 may perform the $StO_2$ measurement and output the data corresponding to the $StO_2$ measurement to processing circuitry 14. In some examples, processing circuitry 14 is configured to determine, based on the data indicative of the $StO_2$ measurement, an $StO_2$ value. Processing circuitry 14 may add the $StO_2$ value to a set of $StO_2$ values as a part of a group of low-quality $StO_2$ values, since the $StO_2$ measurement producing the $StO_2$ value is performed under sub-optimal conditions.

Additionally, in such examples, processing circuitry 14 is configured to determine to output the instruction directing IMD 10 to perform an $StO_2$ measurement if the motion level is less than the threshold motion level, if the amount of ambient light is less than the threshold amount of ambient light, and if processing circuitry 14 determines that the optical test signal is adequate. Processing circuitry 14 may determine that an $StO_2$ measurement performed under such conditions may be predictive of a high-quality $StO_2$ value.

Subsequently, IMD 10 may perform the $StO_2$ measurement and output the data corresponding to the $StO_2$ measurement to processing circuitry 14. Processing circuitry 14 is configured to determine, based on the data indicative of the $StO_2$ measurement, an $StO_2$ value. Processing circuitry 14 may add the $StO_2$ value to a set of $StO_2$ values as a part of a group of high-quality $StO_2$ values, since the $StO_2$ measurement producing the $StO_2$ value is performed under optimal conditions.

It may be beneficial, in some cases, to sort $StO_2$ values into a group of high-quality $StO_2$ values and a group of low-quality $StO_2$ values so that processing circuitry 14 may analyze the group of high-quality $StO_2$ values to identify or monitor patient conditions while excluding the group of low-quality $StO_2$ values. Additionally, in some cases, it may be beneficial to avoid using IMD 10 to perform $StO_2$ measurements that may produce low-quality $StO_2$ values. In other words, processing circuitry 14 may output instructions to perform $StO_2$ measurements after performing the evaluation to determine that conditions are conducive for obtaining a high-quality $StO_2$ value.

In some examples, processing circuitry 14 is configured to determine not to output the instruction directing IMD 10 to perform an $StO_2$ measurement if the motion level is greater than or equal to the threshold motion level, if the amount of ambient light is greater than or equal to the threshold amount of ambient light, or if processing circuitry 14 determines that the optical test signal is not adequate. In some examples, processing circuitry 14 may be configured to determine to output the instruction directing IMD 10 to perform an $StO_2$ measurement if the motion level is less than the threshold motion level, if the amount of ambient light is less than the threshold amount of ambient light, and if processing circuitry 14 determines that the optical test signal is adequate. In this way, processing circuitry 14 is configured to direct IMD 10 to proceed with conducting an $StO_2$ measurement if an amount of ambient light is sufficiently low and the patient motion level is sufficiently low, thus preventing IMD 10 from using energy to produce a less accurate $StO_2$ value. Additionally, processing circuitry 14 may determine whether to output the instruction directing IMD 10 to perform an $StO_2$ measurement based on one or more patient parameters other than an amount ambient light present in tissue and a patient motion level. The one or more patient parameters may include a temperature of an area of tissue, patient posture, a respiration rate, a heart rate, an impedance associated with electrodes of IMD 10, or any combination thereof. By analyzing additional parameters when evaluating whether to proceed with the $StO_2$ measurement, the processing circuitry may reduce a variability in the conditions in which $StO_2$ measurements are taken, thus decreasing an amount of noise in $StO_2$ measurements taken by IMD 10.

In some such examples where the motion level is lower than the threshold motion level, the amount of ambient light is lower than the threshold amount of ambient light, and processing circuitry 14 determines that the optical test signal is adequate, processing circuitry 14 may be configured to output the instruction to IMD 10 to perform the $StO_2$ measurement, causing IMD 10 to perform the $StO_2$ measurement. Subsequently, IMD 10 may perform the $StO_2$ measurement and export data corresponding to the $StO_2$ measurement to processing circuitry 14.

In some examples, to perform an $StO_2$ measurement, IMD 10 may use the optical sensor to obtain a sequence $StO_2$ samples at a sampling frequency within a range from 2 Hz to 10 Hz. In some examples, a duration of the sequence is within a range from 2 seconds to 15 seconds. Subsequently, processing circuitry of IMD 10 may calculate a standard deviation of the samples, and based on the standard deviation, calculate a precision value. Additionally, IMD 10 may determine a number of $StO_2$ samples (N) associated with the calculated precision value, where N represents a minimum number of $StO_2$ samples that must be taken by IMD 10 during the $StO_2$ measurement in order for IMD 10 to determine that the $StO_2$ measurement is adequate. In some examples, IMD 10 may associate a lower number N with a lower precision value and associate a higher number N with a higher precision value. If the sequence of $StO_2$ samples is greater than or equal to N samples in length, IMD 10 may determine that the $StO_2$ measurement is adequate and send the sequence of $StO_2$ samples to processing circuitry 14. If the sequence of $StO_2$ samples is less than N samples in length, IMD 10 may determine that the $StO_2$ measurement is not adequate, and IMD 10 may obtain an additional sequence of $StO_2$ samples, where the additional sequence of $StO_2$ samples includes N samples. Subsequently, IMD 10 may send the additional sequence of $StO_2$ samples to processing circuitry 14 for analysis. IMD 10 may, in some cases, store the value N in a storage device of IMD 10 for future reference. IMD 10 may perform a subsequent $StO_2$ measurement such that an initial sequence of $StO_2$ samples taken during the subsequent $StO_2$ measurement is N samples in length.

After receiving the data corresponding to the $StO_2$ measurement (e.g., the sequence of $StO_2$ samples that IMD 10 deems to be adequate), processing circuitry 14 is configured to determine an $StO_2$ value associated with patient 4. In some examples, processing circuitry 14 determines the $StO_2$ value by calculating a mean or median of the sequence of $StO_2$ samples corresponding to the respective $StO_2$ measurement. The $StO_2$ value may, in some cases be one value of a set of $StO_2$ values each corresponding to a separate $StO_2$ measurement. Processing circuitry 14 may add the $StO_2$ value to the set of tissue oxygen saturation values, which may be stored in a storage device of IMD 10, external device 12, another device in communication with processing circuitry 14, or any combination thereof.

The set of $StO_2$ values may be analyzed to identify or monitor a patient condition. For example, based on the set of $StO_2$ values, processing circuitry 14 may identify a trend of $StO_2$ values. The trend, in some cases, may be a linear best fit curve, an exponential best fit curve, a logarithmic best fit curve, or another type of best fit model. In some cases, the trend of $StO_2$ values may be represented by an indication of whether $StO_2$ values are increasing, decreasing, or generally remaining the same over a period of time. Since processing circuitry, in some cases, is configured to sort $StO_2$ values into a group of high-quality $StO_2$ values and a group of low-quality $StO_2$ values, it may be beneficial to identify the trend of $StO_2$ values based on the group of high-quality $StO_2$ values—while excluding the group of low-quality $StO_2$ values. In this way, processing circuitry 14 may decrease an amount of variability in the trend of $StO_2$ values caused by conditions such as ambient light and patient motion and increase a probability that the trend of $StO_2$ values may be used to identify or monitor a patient condition. After processing circuitry 14 adds a new high-quality $StO_2$ value to the set of $StO_2$ values, processing circuitry 14 may be configured to determine whether the trend of $StO_2$ values is stable. In order to determine trend stability, processing circuitry 14 may be configured to compare the trend of $StO_2$ values with a threshold trend in order to identify whether the group of high-quality $StO_2$ values are changing over a period of time (or other means to detect a meaningful change).

Additionally, in some cases, processing circuitry 14 may determine trend stability by comparing the most recent high-quality $StO_2$ value with a threshold $StO_2$ value. If the most recent high-quality $StO_2$ value is lower than the threshold $StO_2$ value, processing circuitry 14 may determine that the trend is not stable. In some examples, the threshold $StO_2$ value represents a mean $StO_2$ value over a period of time (e.g., a week or a month).

If processing circuitry 14 determines that the trend of $StO_2$ values is stable, indicating that there is no meaningful change in the group of high-quality $StO_2$ values, then may be unlikely $SpO_2$ has changed, and the processing circuitry 14 may return to evaluating whether it is time to perform an evaluation to monitor potentially noise-inducing conditions.

If processing circuitry 14 determines that the trend of $StO_2$ values is not stable, indicating that there is a meaningful change in the group of high-quality $StO_2$ values, processing circuitry 14 may output an instruction to perform an $SpO_2$ measurement. In some examples, processing circuitry 14 outputs the instruction to perform the $SpO_2$ measurement in order to confirm that the instability of the trend of $StO_2$ values is caused by an instability of $SaO_2$ in patient 4—and not an instability of another parameter, such as $SvO_2$. In some examples, processing circuitry 14 outputs the instruction to perform the $SpO_2$ measurement to IMD 10. In some such examples, IMD 10 performs the $SpO_2$ measurement and sends data corresponding to the $SpO_2$ measurement to processing circuitry 14. In other examples, processing circuitry 14 outputs the instruction to perform the $SpO_2$ measurement to a device (e.g., a fingertip pulse oximeter, a smart phone, or a desktop base station) other than IMD 10 that is configured for performing $SpO_2$ measurements. The device may perform the $SpO_2$ measurement and send data corresponding to the $SpO_2$ measurement to processing circuitry 14. In either case, processing circuitry 14 may receive the data corresponding to the $SpO_2$ measurement. Based on the data corresponding to the $SpO_2$ measurement, processing circuitry 14 may determine an $SpO_2$ value.

In examples where IMD 10 performs the $SpO_2$ measurement using the optical sensor, the $SpO_2$ measurement may consume significantly more energy than a $StO_2$ measurement. For example, an $SpO_2$ measurement may consume up to three orders of magnitude (1,000 times) more energy than an $StO_2$ measurement. As such, it may be important to limit a number of $SpO_2$ measurements taken by IMD 10. For example, processing circuitry 14 may instruct IMD 10 to perform an $SpO_2$ measurement when processing circuitry 14 determines that there is a high likelihood that a patient condition is worsening. (e.g., when processing circuitry 14 identifies an unstable or decreasing trend of $StO_2$ values). In some examples, processing circuitry 14 may instruct a pulse oximetry device other than IMD 10 to perform the $SpO_2$ measurement in order to save charge in the power source of IMD 10.

After processing circuitry 14 determines the $SpO_2$ value corresponding to the $SpO_2$ measurement, processing circuitry 14 may determine whether the trend of $StO_2$ values is not stable due to an instability of $SaO_2$ in patient 4, or if the trend of $StO_2$ values is not stable because of a parameter other than $SaO_2$ (e.g., $SvO_2$). In both cases where the trend of $StO_2$ values is not stable because of a parameter other than $SaO_2$ and cases where the trend of $StO_2$ values is not stable because of an instability of $SaO_2$ in patient 4, processing circuitry 14 may determine that the trend of $StO_2$ values indicates a worsening of a patient condition (e.g., heart failure). In turn, processing circuitry 14 may output an alert that the patient condition is worsening. In some examples, processing circuitry 14 may output the alert to external device 12, or another external device that may be accessed by patient 4 or a clinician.

External device 12 may be used to program commands or operating parameters into IMD 10 for controlling its functioning (e.g., when configured as a programmer for IMD 10). In some examples, external device 12 may be used to interrogate IMD 10 to retrieve data, including device operational data as well as physiological data accumulated in IMD memory. Such interrogation may occur automatically according to a schedule, or may occur in response to a remote or local user command. Programmers, external monitors, and consumer devices are examples of external device 12 that may be used to interrogate IMD 10. Examples of communication techniques used by IMD 10 and external device 12 include radiofrequency (RF) telemetry, which may be an RF link established via Bluetooth®, Near Field Communication (NFC), WiFi, or medical implant communication service (MICS). In some examples, external device 12 may include a user interface configured to allow a clinician to remotely interact with IMD 10.

IMD 10 may be configured to monitor more periodic signals indicating patient status, using those signals to identify a "template" or "signature" period during which the optical signals are most repeatable and representative of a systemic status and/or trending of patient 4's condition. For example, a temperature of a patient 4 in a subcutaneous space relatively close to the skin may be regulated by an external environment and thermal regulation via vasodilation to control blood flow. For example, in a hot environment, patient 4's autonomic system may vasodilate blood vessels to increase blood flow, thus increasing thermal transport from the core body to the environment. Likewise, in a cold environment, patient 4's autonomic system may vasoconstrict blood vessels near the skin to restrict heat flow to the environment, and conserve core body temperature. Vasodilation and vasoconstriction change both an overall net flow of blood and a metabolic oxygen exchange balance, which may affect measurements performed using the optical sensor of IMD 10. Vasodilation and vasoconstriction, in some cases, may be determined, at least in part, based on THI. Also, a surface temperature of patient 4 may change according to a daily cycle corresponding with a cycle of sleeping and being awake, among other physiological factors.

After IMD 10 is implanted in patient 4, a temperature sensor of IMD 10 may measure patient 4's temperature in intervals (e.g., once every 1-30 minutes) for a period of time lasting, for example, between 1 week and 8 weeks. IMD 10 may aggregate and analyze the temperature data to determine a representative temperature baseline. In some examples, processing circuitry 14 may use the representative temperature baseline when conducting an evaluation to determine whether to output an instruction to IMD 10 directing IMD 10 to perform an $StO_2$ measurement. For example, to conduct the evaluation, processing circuitry 14 may instruct IMD 10 to measure patient 4's temperature and compare the measured temperature with the representative temperature baseline. Based on the comparison, processing circuitry 14 may determine whether to output the instruction to perform the $StO_2$ measurement. The representative temperature baseline may include one of several stochastic measures. For example, the representative temperature baseline may be represented by a range around a mean baseline temperature or a median baseline temperature. In some examples, optical sensor signals are known to yield better SNR at elevated temperatures due to the increased blood flow. As such, in some cases, the representative temperature baseline may be represented by a range around a higher temperature, such as an $80^{th}$ percentile temperature.

In some examples, an infection may cause patient 4's core body temperature to increase over time. Additionally, in some examples, conditions such as internal bleeding or progressing heart failure may cause vasoconstriction on the periphery. In these examples, the changing trend in temperature may be reported as diagnostic information, and also be used to adjust criterion for optical sensor measurement.

Signals such as patient posture, respiration, heart rate, heart rate variability, and impedance may be used individually or in aggregate to determine whether to perform measurements using the optical sensor of IMD 10. For example, processing circuitry 14 may direct IMD 10 to take a set of $StO_2$ measurements, where patient 4 is largely under the same conditions each time when each $StO_2$ measurement of the set of $StO_2$ measurements is taken. In other words, processing circuitry 14 may evaluate one or more of patient posture, respiration, heart rate, heart rate variability, and impedance, and THI indicating vasodilation or vasoconstriction before each $StO_2$ measurement to ensure that the values of such parameters remain relatively constant across the set of $StO_2$ measurements. In some examples, processing circuitry 14 may automatically monitor for periods when patient 4 is at rest for a period of time (indicated by respiration, heart rate, and heart rate variability), when patient 4 is supine, when patient 4 is prone (indicated by posture sensing), similar interstitial fluid status (indicated by impedance), similar temperature, or any combination thereof. In some examples, processing circuitry 14 may output an instruction to perform a measurement using the optical sensor at the same point during each respiration cycle of a set of respiration cycles.

Additionally, these signals (e.g., patient posture, respiration, heart rate, heart rate variability, impedance, and/or THI) may be used to classify $StO_2$ measurements performed by IMD 10. For example, around a time in which IMD 10 performs an $StO_2$ measurement, IMD 10 may additionally measure a set of parameter values (e.g., the signals) and associate the set of parameter values with the $StO_2$ measurement. In some cases, each $StO_2$ measurement of a set of $StO_2$ measurements may be associated with a respective set of parameter values. In this way, processing circuitry 14 may analyze the set of $StO_2$ measurements based on the respective sets of parameter values in order to reduce a variability in conditions associated with $StO_2$ measurements. In some examples, the sets of parameter values and the set of $StO_2$ measurements may be inputs to a machine learning algorithm which outputs an analysis of the set of $StO_2$ measurements based on the respective sets of parameter values.

In some examples, if patient 4 has COPD or sleep apnea, medical device system 2 may monitor for an increasing heart rate over a period of time. However, in some cases, physical activity, stress, or other factors may induce a similar increase in heart rate. In such cases, the optical sensor of IMD 10 may be interrogated to confirm whether the increase in heart rate is related to COPD or sleep apnea.

In general, reducing the influence of physiologic variability by monitoring for several patient parameters may enhance an ability of medical device system 2 to identify or monitor patient conditions.

Medical device system 2 is an example of a medical device system configured to identify or monitor one or more conditions of patient 4. At least some of the techniques described herein may be performed by processing circuitry 14 of a device of medical device system 2. In some examples, processing circuitry 14 may include processing circuitry of IMD 10, processing circuitry of external device 12, and/or by processing circuitry of one or more other implanted or external devices or servers not shown. Examples of the one or more other implanted or external devices may include a transvenous, subcutaneous, or extravascular pacemaker or implantable cardioverter-defibrillator (ICD), a blood analyzer, an external monitor, a drug pump, or an external pulse oximetry device. The communication circuitry of each of the devices of medical device system 2 allows the devices to communicate with one another. In addition, although the optical sensors and electrodes are described herein as being positioned on a housing of IMD 10, in other examples, such optical sensors and/or electrodes may be positioned on a housing of another device not illustrated in FIG. 1 that is implanted in patient 4, such as a transvenous, subcutaneous, or extravascular pacemaker or ICD, or coupled to such a device by one or more leads.

Additionally, or alternatively, in some examples, the optical sensors and/or electrodes may be positioned on a device external to patient 4 such as a Bluetooth® finger pulse oximeter, an activity watch, a smart phone, or any combination thereof. The external device may also include blood gas analyzers or chemical sensors that require blood samples extracted from the patient, or invasive monitors such as arterial lines to measure blood pressure or Swan-Ganz catheters. In such examples, one or more of IMD 10 and external device 12 may include processing circuitry configured to receive signals from the electrodes or optical sensors (e.g., via a Bluetooth® antenna). In some examples, IMD 10 may include a longer housing and may be configured to measure a patient ECG. In other examples, IMD 10 may include a shorter housing and measure optical signals.

In some examples, medical device system 2 may be configured to monitor one or more parameters in addition to or instead of any of, $StO_2$, $SpO_2$, patient motion level, patient posture, ambient light level, optical signal quality, impedance, heart rate, heart rate variability, respiration rate, pulse transit time, and temperature. For example, sensors on IMD 10 or one or more other implanted or external devices may be configured to sense signals associated with such parameters. Such one or more parameters may be associated with physiological functions of patient 4, such as kidney function, which may change when patient condition (e.g., heart failure) of patient 4 changes. For example, one or more implanted or external devices of medical device system 2 (e.g., IMD 10) may include one or more sensors configured to sense blood or tissue levels of one or more compounds associated with kidney function of patient 4, such as creatinine or blood urea nitrogen. In some examples, such one or more parameters may not be directly associated with changes in a status of a patient condition, but may provide other information about the health of patient 4, such as motion levels or sleep patterns.

Figure 2:
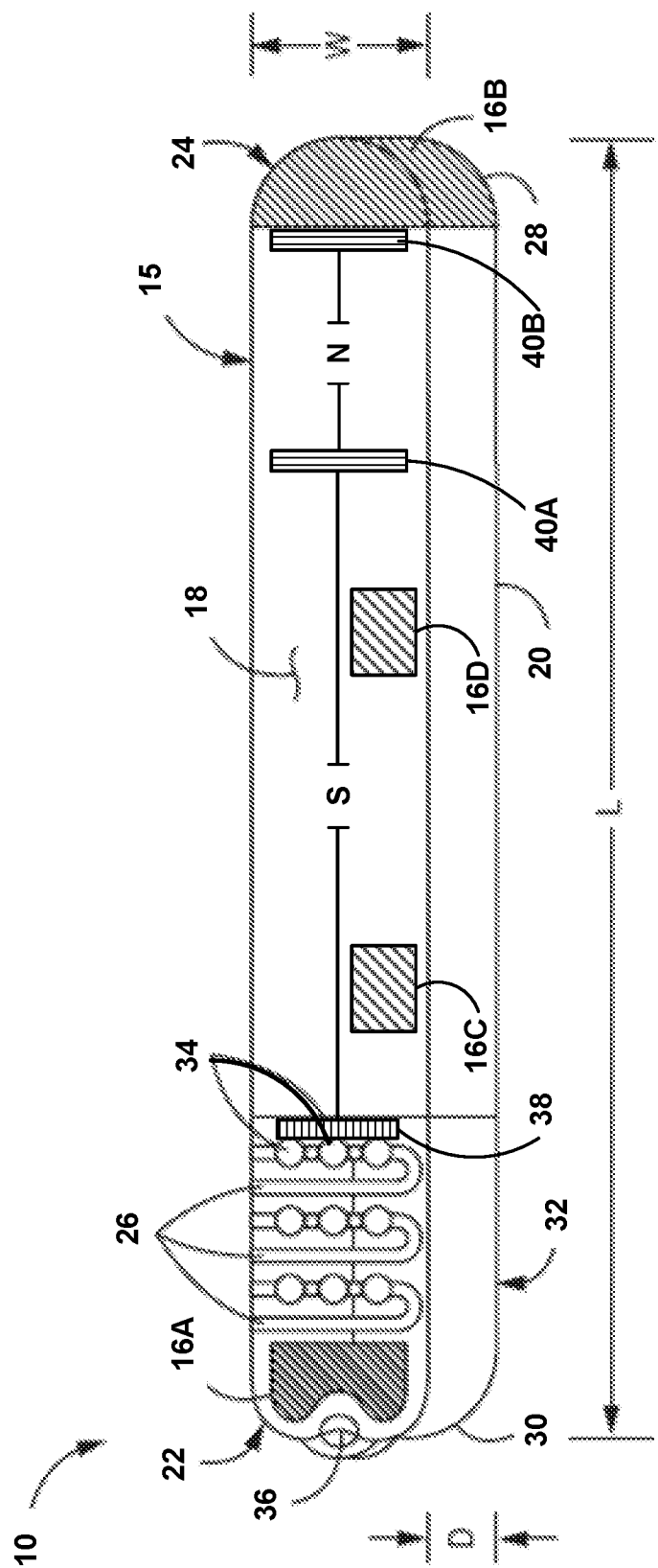
FIG. 2 is a conceptual drawing illustrating an example configuration of the IMD of the medical device system of FIG. 1, in accordance with one or more techniques described herein.
Figure 3:
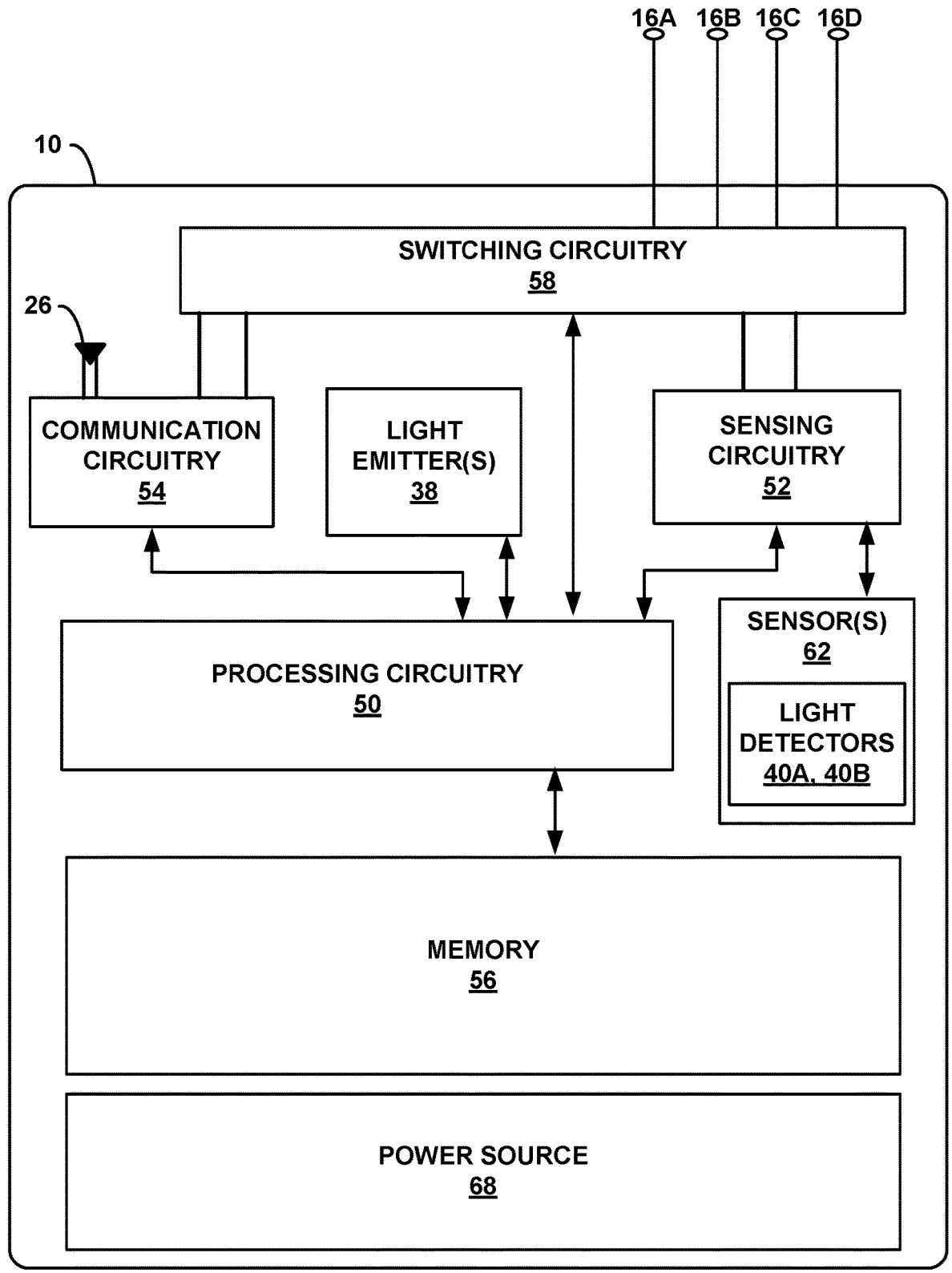
FIG. 3 is a functional block diagram illustrating an example configuration of the IMD of FIGS. 1 and 2, in accordance with one or more techniques described herein.
Figure 4A:
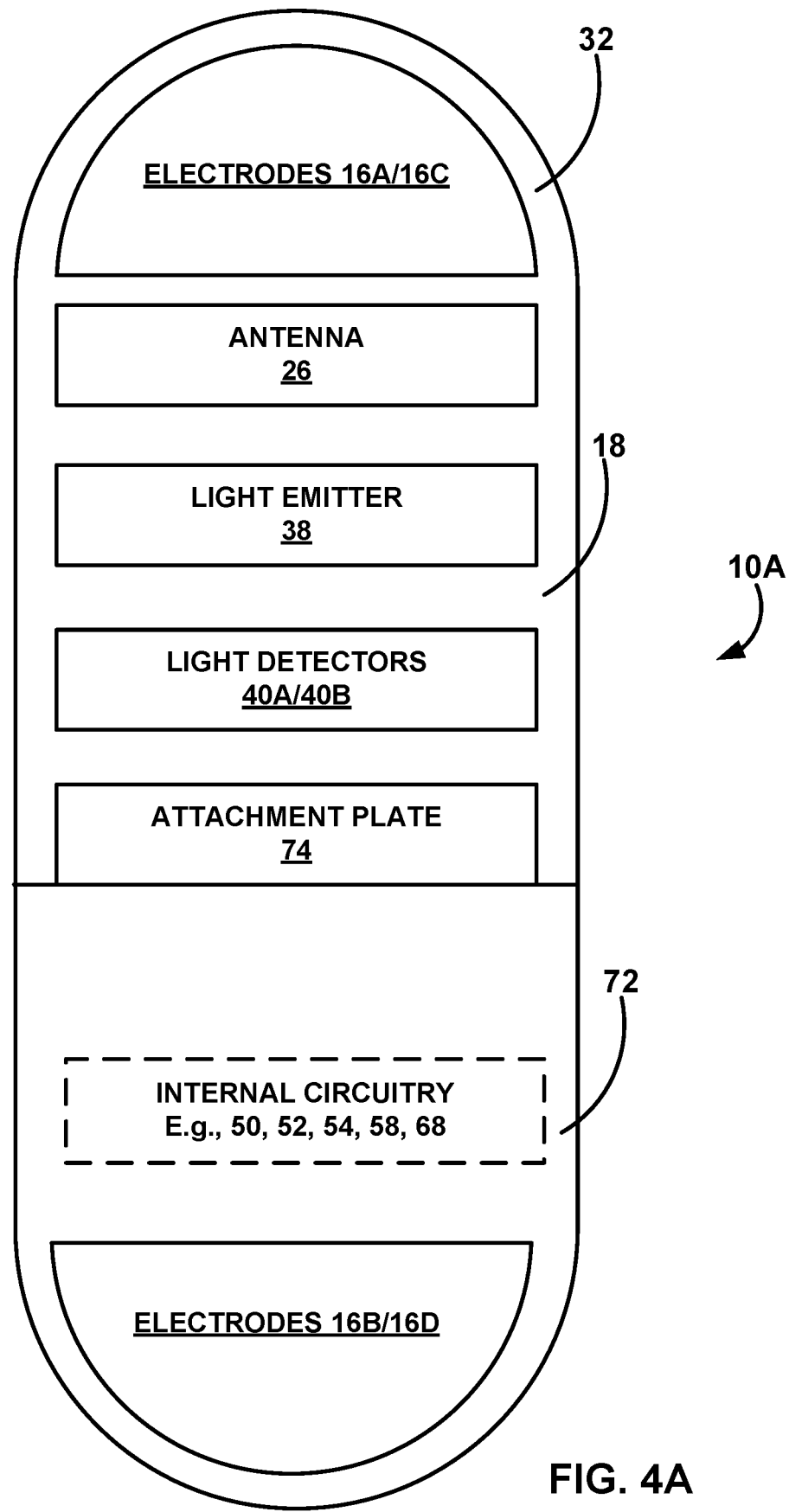

FIGS. 2-4B illustrate various aspects and example arrangements of IMD 10 of FIG. 1. For example, FIG. 2 conceptually illustrates an example physical configuration of IMD 10. FIG. 3 is a block diagram illustrating an example functional configuration of IMD 10. FIGS. 4A and 4B illustrate additional views of an example physical and functional configuration of IMD 10. It should be understood that any of the examples of IMD 10 described below with respect to FIGS. 2-4B may be used to implement the techniques described herein for determining whether to perform parameter measurements using IMD 10. IMD 10 may concurrently collect sensor signals and parameter measurements. For example, compiled data may be used for model fitting and other means of Artificial Intelligence to assess and predict a trajectory of a patient condition. Additionally, compiled data may be used to categorize or group parameter measurements of IMD 10. Some measurements made by of IMD 10 may be used to categorize or group other measurements.

FIG. 2 is a conceptual drawing illustrating an example configuration of IMD 10 of the medical device system 2 of FIG. 1, in accordance with one or more techniques described herein. In the example shown in FIG. 2, IMD 10 may include a leadless, subcutaneously-implantable monitoring device having housing 15, proximal electrode 16A, and distal electrode 16B. housing 15 may further include first major surface 18, second major surface 20, proximal end 22, and distal end 24. In some examples, IMD 10 may include one or more additional electrodes 16C, 16D positioned on one or both of major surfaces 18, 20 of IMD 10. Housing 15 encloses electronic circuitry located inside the IMD 10, and protects the circuitry contained therein from fluids such as body fluids. In some examples, electrical feedthroughs provide electrical connection of electrodes 16A-16D, and antenna 26, to circuitry within housing 15. In some examples, electrode 16B may be formed from an uninsulated portion of conductive housing 15.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape) along a longitudinal axis of IMD 10, which may help maintain the device in a desired orientation following implantation.

In some examples, a spacing between proximal electrode 16A and distal electrode 16B may range from about 30-55 millimeters (mm), about 35-55 mm, or about 40-55 mm, or more generally from about 25-60 mm. Overall, IMD 10 may have a length L of about 20-30 mm, about 40-60 mm, or about 45-60 mm. In some examples, the width W of major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle. In some examples, a housing of IMD 10 is configured for ECG measurements. Additionally, in some examples, a housing of IMD 10 is configured for for optical sensing. A housing configured for optical sensing may be significantly smaller than a housing configured for ECG sensing, and the housing configured for optical sensing may be implanted in different regions throughout the body of patient 4 than the housing configured for ECG sensing.

IMD 10, according to an example of the present disclosure, may have a geometry and size designed for ease of implant and patient comfort. Examples of IMD 10 described in this disclosure may have a volume of 3 cubic centimeters (cm$^3$) or less, 1.5 cm$^3$ or less, or any volume therebetween.

In addition, in the example shown in FIG. 2, proximal end 22 and distal end 24 are rounded to reduce discomfort and irritation to surrounding tissue once implanted under the skin of patient 4. In some examples, power may be supplied to IMD 10 through inductive coupling.

In some examples, first major surface 18 of IMD 10 faces outward towards the skin, when IMD 10 is inserted within patient 4, whereas second major surface 20 is faces inward toward musculature of patient 4. Thus, first and second major surfaces 18, 20 may face in directions along a sagittal axis of patient 4 (see FIG. 1), and this orientation may be maintained upon implantation due to the dimensions of IMD 10. In some examples, first major surface 18 faces inward towards the musculature of patient 4, and second major surface 20 faces outward towards the skin of patient 4.

Proximal electrode 16A and distal electrode 16B may be used to sense cardiac EGM signals (e.g., ECG signals) when IMD 10 is implanted subcutaneously in patient 4. Processing circuitry 14 may determine a pulse transit time value based in part on cardiac ECG signals, as further described below. In some examples, processing circuitry of IMD 10 also may determine whether cardiac ECG signals of patient 4 are indicative of arrhythmia or other abnormalities, which processing circuitry of IMD 10 may evaluate in determining whether a condition (e.g., heart failure) of patient 4 has changed. The cardiac ECG signals may be stored in a memory of the IMD 10, and data derived from the cardiac ECG signals may be transmitted via integrated antenna 26 to another medical device, such as external device 12. In some examples, one or both of electrodes 16A and 16B also may be used to detect a subcutaneous impedance value for assessing a congestion status of patient 4, monitoring one or more respiratory parameters (e.g., respiration rate, respiration rate variability respiration effort, and relative tidal volume), and/or may be used by communication circuitry of IMD 10 for tissue conductance communication (TCC) with external device 12. In some examples, ECG and/or impedance signals obtained by electrodes 16A and 16B may be used to determine one or more respiratory parameters (e.g., respiration rate, respiration rate variability, respiration effort, or relative tidal volume).

In the example shown in FIG. 2, proximal electrode 16A is in close proximity to proximal end 22, and distal electrode 16B is in close proximity to distal end 24 of IMD 10. In this example, distal electrode 16B is not limited to a flattened, outward facing surface, but may extend from first major surface 18, around rounded edges 28 or end surface 30, and onto the second major surface 20 in a three-dimensional curved configuration. As illustrated, proximal electrode 16A is located on first major surface 18 and is substantially flat and outward facing. However, in other examples not shown here, proximal electrode 16A and distal electrode 16B both may be configured like proximal electrode 16A shown in FIG. 2, or both may be configured like distal electrode 16B shown in FIG. 2. In some examples, additional electrodes 16C and 16D may be positioned on one or both of first major surface 18 and second major surface 20, such that a total of four electrodes are included on IMD 10. Any of electrodes 16A-16D may be formed of a biocompatible conductive material. For example, any of electrodes 16A-16D may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used.

In the example shown in FIG. 2, proximal end 22 of IMD 10 includes header assembly 32 having one or more of proximal electrode 16A, integrated antenna 26, anti-migration projections 34, and suture hole 36. Integrated antenna 26 is located on the same major surface (e.g., first major surface 18) as proximal electrode 16A, and may be an integral part of header assembly 32. In other examples, integrated antenna 26 may be formed on the major surface opposite from proximal electrode 16A, or, in still other examples, may be incorporated within housing 15 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, NFC, Radio Frequency Identification (RFID), Bluetooth®, WiFi, or other proprietary or non-proprietary wireless telemetry communication schemes. Antenna 26 may be coupled to communication circuitry of IMD 10, which may drive antenna 26 to transmit signals to external device 12, and may transmit signals received from external device 12 to processing circuitry of IMD 10 via communication circuitry.

IMD 10 may include several features for retaining IMD 10 in position once subcutaneously implanted in patient 4. For example, as shown in FIG. 2, housing 15 may include anti-migration projections 34 positioned adjacent integrated antenna 26. Anti-migration projections 34 may include a plurality of bumps or protrusions extending away from first major surface 18, and may help prevent longitudinal movement of IMD 10 after implantation in patient 4. In other examples, anti-migration projections 34 may be located on the opposite major surface as proximal electrode 16A and/or integrated antenna 26. In addition, in the example shown in FIG. 2 header assembly 32 includes suture hole 36, which provides another means of securing IMD 10 to the patient to prevent movement following insertion. In the example shown, suture hole 36 is located adjacent to proximal electrode 16A. In some examples, header assembly 32 may include a molded header assembly made from a polymeric or plastic material, which may be integrated or separable from the main portion of IMD 10.

In some examples, processing circuitry of IMD 10 may determine a subcutaneous tissue impedance value of patient 4 based on signals received from at least two of electrodes 16A-16D. For example, processing circuitry of IMD 10 may generate one of a current or voltage signal, deliver the signal via a selected two or more of electrodes 16A-16D, and measure the resulting other of current or voltage. Processing circuitry of IMD 10 may determine an impedance signal based on the delivered current or voltage and the measured voltage or current.

In the example shown in FIG. 2, IMD 10 includes light emitter(s) 38 and a proximal light detector 40A and a distal light detector 40B (collectively, "light detectors 40") positioned on housing 15 of IMD 10. Light detector 40A may be positioned at a distance S from light emitter(s) 38, and a distal light detector 40B positioned at a distance S+N from light emitter(s) 38. In other examples, IMD 10 may include only one of light detectors 40A, 40B, or may include additional light emitters and/or additional light detectors. Collectively, light emitter(s) 38 and light detectors 40A, 40B may include an optical sensor, which may be used in the techniques described herein to determine $StO_2$ or $SpO_2$ values of patient 4. Although light emitter(s) 38 and light detectors 40A, 40B are described herein as being positioned on housing 15 of IMD 10, in other examples, one or more of light emitter(s) 38 and light detectors 40A, 40B may be positioned, on a housing of another type of IMD within patient 4, such as a transvenous, subcutaneous, or extravascular pacemaker or ICD, or connected to such a device via a lead. Light emitter(s) 38 include a light source, such as an LED, that may emit light at one or more wavelengths within the visible (VIS) and/or near-infrared (NIR) spectra. For example, light emitter(s) 38 may emit light at one or more of about 660 nanometer (nm), 720 nm, 760 nm, 800 nm, or at any other suitable wavelengths.

In some examples, techniques for determining $StO_2$ may include using light emitter(s) 38 to emit light at one or more VIS wavelengths (e.g., approximately 660 nm) and at one or more NIR wavelengths (e.g., approximately 850-890 nm). The combination of VIS and NIR wavelengths may help enable processing circuitry of IMD 10 to distinguish oxygenated hemoglobin from deoxygenated hemoglobin in the tissue of patient 4, since as hemoglobin becomes less oxygenated, an attenuation of VIS light increases and an attenuation of NIR decreases. By comparing the amount of VIS light detected by light detectors 40A, 40B to the amount of NIR light detected by light detectors 40A, 40B, processing circuitry of IMD 10 may determine the relative amounts of oxygenated and deoxygenated hemoglobin in the tissue of patient 4. For example, if the amount of oxygenated hemoglobin in the tissue of patient 4 decreases, the amount of VIS light detected by light detectors 40A, 40B increases and the amount of NIR light detected by light detectors 40A, 40B decreases. Similarly, if the amount of oxygenated hemoglobin in the tissue of patient 4 increases, the amount of VIS light detected by light detectors 40A, 40B decreases and the amount of NIR light detected by light detectors 40A, 40B increases.

As shown in FIG. 2, light emitter(s) 38 may be positioned on header assembly 32, although, in other examples, one or both of light detectors 40A, 40B may additionally or alternatively be positioned on header assembly 32. In some examples, light emitter(s) 38 may be positioned on a medial section of IMD 10, such as part way between proximal end 22 and distal end 24. Although light emitter(s) 38 and light detectors 40A, 40B are illustrated as being positioned on first major surface 18, light emitter(s) 38 and light detectors 40A, 40B alternatively may be positioned on second major surface 20. In some examples, IMD may be implanted such that light emitter(s) 38 and light detectors 40A, 40B face inward when IMD 10 is implanted, toward the muscle of patient 4, which may help minimize interference from background light coming from outside the body of patient 4. Light detectors 40A, 40B may include a glass or sapphire window, such as described below with respect to FIG. 4B, or may be positioned beneath a portion of housing 15 of IMD 10 that is made of glass or sapphire, or otherwise transparent or translucent.

Light emitter(s) 38 may emit light into a target site of patient 4 during a technique for determining an $StO_2$ value of patient 4. The target site may generally include the interstitial space around IMD 10 when IMD 10 is implanted in patient 4. Light emitter(s) 38 may emit light directionally in that light emitter(s) 38 may direct the signal to a side of IMD 10, such as when light emitter(s) 38 are disposed on the side of IMD 10 that includes first major surface 18. The target site may include the subcutaneous tissue adjacent IMD 10 within patient 4.

Techniques for determining an $StO_2$ value may be based on the optical properties of blood-perfused tissue that change depending upon the relative amounts of oxygenated and deoxygenated hemoglobin in the microcirculation of tissue. These optical properties are due, at least in part, to the different optical absorption spectra of oxygenated and deoxygenated hemoglobin. Thus, the oxygen saturation level of the patient's tissue may affect the amount of light that is absorbed by blood within the tissue adjacent IMD 10, and the amount of light that is reflected by the tissue. Light detectors 40A, 40B each may receive light from light emitter(s) 38 that is reflected by the tissue, and generate electrical signals indicating the intensities of the light detected by light detectors 40A, 40B. Processing circuitry of IMD 10 then may evaluate the electrical signals from light detectors 40A, 40B in order to determine an $StO_2$ value of patient 4.

In some examples, a difference between the electrical signals generated by light detectors 40A, 40B may enhance an accuracy of the $StO_2$ value determined by IMD 10. For example, because tissue absorbs some of the light emitted by light emitter(s) 38, the intensity of the light reflected by tissue becomes attenuated as the distance (and amount of tissue) between light emitter(s) 38 and light detectors 40A, 40B increases. Thus, because light detector 40B is positioned further from light emitter(s) 38 (at distance S+N) than light detector 40A (at distance S), the intensity of light detected by light detector 40B should be less than the intensity of light detected by light detector 40A. Due to the close proximity of detectors 40A, 40B to one another, the difference between the intensity of light detected by light detector 40A and the intensity of light detected by light detector 40B should be attributable only to the difference in distance from light emitter(s) 38. In some examples, processing circuitry of IMD 10 may use the difference between the electrical signals generated by light detectors 40A, 40B, in addition to the electrical signals themselves, in determining an $StO_2$ value of patient 4.

In some examples, IMD 10 may include one or more additional sensors, such as one or more accelerometers (not shown). Such accelerometers may be 3D accelerometers configured to generate signals indicative of one or more types of movement of the patient, such as gross body movement (e.g., activity) of the patient, patient posture, movements associated with the beating of the heart, or coughing, rales, or other respiration abnormalities. Additionally, or alternatively, one or more of the parameters monitored by IMD 10 may fluctuate in response to changes in one or more such types of movement. For example, changes in parameter values sometimes may be attributable to increased patient activity (e.g., exercise or other physical activity as compared to inactivity) or to changes in patient posture, and not necessarily to changes in a heart failure status caused by a progression of a heart failure condition. Thus, in some methods of identifying or monitoring a condition of patient 4, it may be advantageous to account for such fluctuations when determining whether a change in a patient parameter is indicative of a change in a condition of patient 4.

In some examples, IMD 10 may perform an $SpO_2$ measurement using light emitter(s) 38 and light detectors 40. For example, IMD 10 may perform $SpO_2$ measurements by using light emitter(s) 38 to emit light at one or more VIS wavelengths, one more NIR wavelengths, or a combination of one or more VIS wavelengths and one more NIR wavelengths. By comparing the amount of VIS light detected by light detectors 40A, 40B to the amount of NIR light detected by light detectors 40A, 40B, processing circuitry of IMD 10 may determine the relative amounts of oxygenated and deoxygenated hemoglobin in the tissue of patient 4. For example, if the amount of oxygenated hemoglobin in the tissue of patient 4 decreases, the amount of VIS light detected by light detectors 40A, 40B increases and the amount of NIR light detected by light detectors 40A, 40B decreases. Similarly, if the amount of oxygenated hemoglobin in the tissue of patient 4 increases, the amount of VIS light detected by light detectors 40A, 40B decreases and the amount of NIR light detected by light detectors 40A, 40B increases.

Although $SpO_2$ measurements and $StO_2$ measurements may both employ the optical sensor (e.g., light emitter(s) 38 and light detectors 40) of IMD 10 to emit and sense light, $SpO_2$ measurements may consume significantly more energy than $StO_2$ measurements. In some examples, an $SpO_2$ measurement may consume up to 3 orders of magnitude (1,000 times) more power than an $StO_2$ measurement. Reasons for the energy consumption disparity include that $SpO_2$ measurements may require light emitter(s) 38 to be activated for up to 30 seconds, where $StO_2$ measurements may require light emitter(s) 38 to be activated for up to 5 seconds. Additionally, $SpO_2$ measurements may require a sampling rate of up to 70 Hz, whereas $StO_2$ measurements may require a sampling rate of up to 4 Hz.

FIG. 3 is a functional block diagram illustrating an example configuration of IMD 10 of FIGS. 1 and 2, in accordance with one or more techniques described herein. In the illustrated example, IMD 10 includes electrodes 16, antenna 26, light emitter(s) 38, processing circuitry 50, sensing circuitry 52, communication circuitry 54, memory 56, switching circuitry 58, sensors 62 including light detectors 40, and power source 68. In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 and communication circuitry 54 may be selectively coupled to electrodes 16A-16D via switching circuitry 58, as controlled by processing circuitry 50. Sensing circuitry 52 may monitor signals from electrodes 16A-16D in order to monitor electrical activity of heart (e.g., to produce an ECG), and/or subcutaneous tissue impedance. Sensing circuitry 52 also may monitor signals from sensors 62, which may include light detectors 40A, 40B, and any additional light detectors that may be positioned on IMD 10. In some examples, sensing circuitry 52 may include one or more filters and amplifiers for filtering and amplifying signals received from one or more of electrodes 16A-16D and/or light detectors 40A, 40B.

Communication circuitry 54 may include any suitable hardware, firmware, software or any combination thereof for communicating with another device, such as external device 12 or another IMD or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In some examples, communication circuitry 54 may communicate with external device 12. In addition, processing circuitry 50 may communicate with a networked computing device via external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device.

Power source 68 is configured to deliver operating power to the components of IMD 10. Power source 68 may include a battery and a power generation circuit to produce the operating power. In some examples, the battery is rechargeable to allow extended operation. In some examples, recharging is accomplished through proximal inductive interaction between an external charger and an inductive charging coil within external device 12. Power source 68 may include any one or more of a plurality of different battery types, such as nickel cadmium batteries and lithium ion batteries. A non-rechargeable battery may be selected to last for several years, while a rechargeable battery may be inductively charged from an external device, e.g., on a daily or weekly basis.

FIGS. 4A and 4B are block diagrams illustrating two additional example IMDs that may be substantially similar to IMD 10 of FIGS. 1-3, but which may include one or more additional features, in accordance with one or more techniques described herein. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 72 and an attachment plate 74. Attachment plate 74 may be configured to mechanically couple header assembly 32 to body portion 72 of IMD 10A. Body portion 72 of IMD 10A may be configured to house one or more of the internal components of IMD 10 illustrated in FIG. 3, such as one or more of processing circuitry 50, sensing circuitry 52, communication circuitry 54, memory 56, switching circuitry 58, and internal components of sensors 62. In some examples, body portion 72 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 76, which may help insulate electrical signals passing between electrodes 16A-16D and/or optical detectors 40A, 40B on housing 15B and processing circuitry 50. In some examples, insulative cover 76 may be positioned over an open housing 15 to form the housing for the components of IMD 10B. One or more components of IMD 10B (e.g., antenna 26, light emitter(s) 38, light detectors 40A, 40B, processing circuitry 50, sensing circuitry 52, communication circuitry 54, switching circuitry 58, or any combination thereof) may be formed on a bottom side of insulative cover 76, such as by using flip-chip technology. Insulative cover 76 may be flipped onto a housing 15B. When flipped and placed onto housing 15B, the components of IMD 10B formed on the bottom side of insulative cover 76 may be positioned in a gap 78 defined by housing 15B.

Insulative cover 76 may be configured so as not to interfere with the operation of IMD 10B. For example, one or more of electrodes 16A-16D may be formed or placed above or on top of insulative cover 76, and electrically connected to switching circuitry 58 through one or more vias (not shown) formed through insulative cover 76. In addition, to enable IMD to determine values of patient parameters (e.g., $StO_2$ and $SpO_2$), at least a portion of insulative cover 76 may transparent to the NIR or visible wavelengths emitted by light emitter(s) 38 and detected by light detectors 40A, 40B, which in some examples may be positioned on a bottom side of insulative cover 76 as described above.

In some examples, light emitter(s) 38 may include an optical filter between light emitter(s) 38 and insulative cover 76, which may limit the spectrum of emitted light to be within a narrow band. Similarly, light detectors 40A, 40B may include optical filters between light detectors 40A, 40B and insulative cover 76, so that light detectors 40A, 40B detects light from a narrow spectrum, generally at longer wavelengths than the emitted spectrum. Other optical elements that may be included in the IMD 10B may include index matching layers, antireflective coatings, or optical barriers, which may be configured to block light emitted sideways by the light emitter(s) 38 from reaching light detectors 40.

Figure 5:
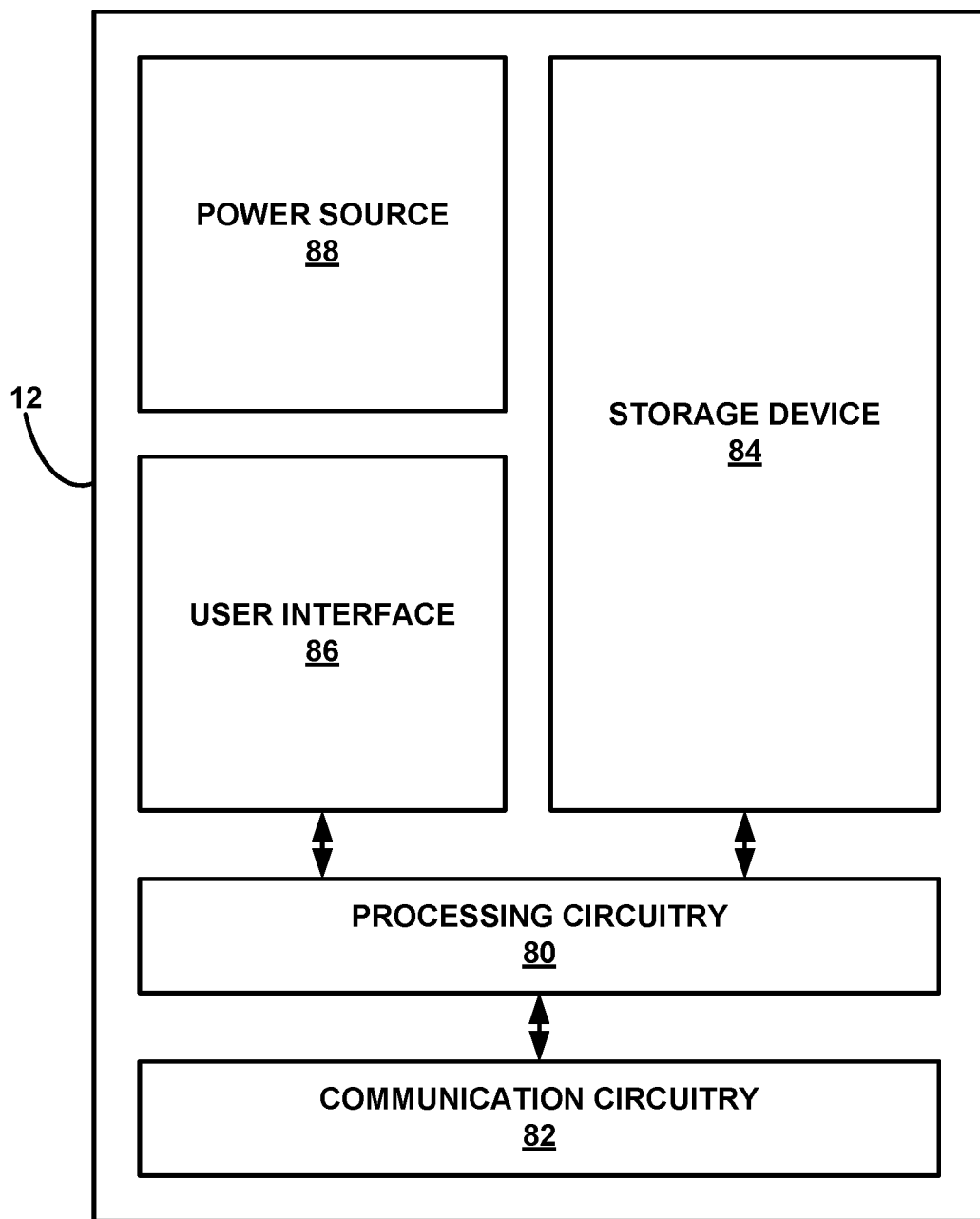
FIG. 5 is a block diagram illustrating an example configuration of components of the external device of FIG. 1, in accordance with one or more techniques of this disclosure.

FIG. 5 is a block diagram illustrating an example configuration of components of external device 12, in accordance with one or more techniques of this disclosure. In the example of FIG. 5, external device 12 includes processing circuitry 80, communication circuitry 82, storage device 84, user interface 86, and power source 88.

Processing circuitry 80, in one example, may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., data corresponding to $StO_2$ measurements, data corresponding to $SpO_2$ measurements, or data corresponding to other parameter measurements) to external device 12. In turn, external device 12 may receive the collected data from IMD 10 and store the collected data in storage device 84. Additionally, or alternatively, processing circuitry 80 may export instructions to IMD 10 requesting IMD 10 to update electrode combinations for stimulation or sensing.

A user, such as a clinician or patient 4, may interact with external device 12 through user interface 86. User interface 86 includes a display (not shown), such as an LCD or LED display or other type of screen, with which processing circuitry 80 may present information related to IMD 10 (e.g., EGM signals obtained from at least one electrode or at least one electrode combination). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to patient 4, receiving voice commands from patient 4, or both. Storage device 84 may include instructions for operating user interface 86 and for managing power source 88.

Power source 88 is configured to deliver operating power to the components of external device 12. Power source 88 may include a battery and a power generation circuit to produce the operating power. In some examples, the battery is rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within external device 12. In other examples, traditional batteries (e.g., nickel cadmium or lithium ion batteries) may be used. In addition, external device 12 may be directly coupled to an alternating current outlet to operate.

Figure 6:
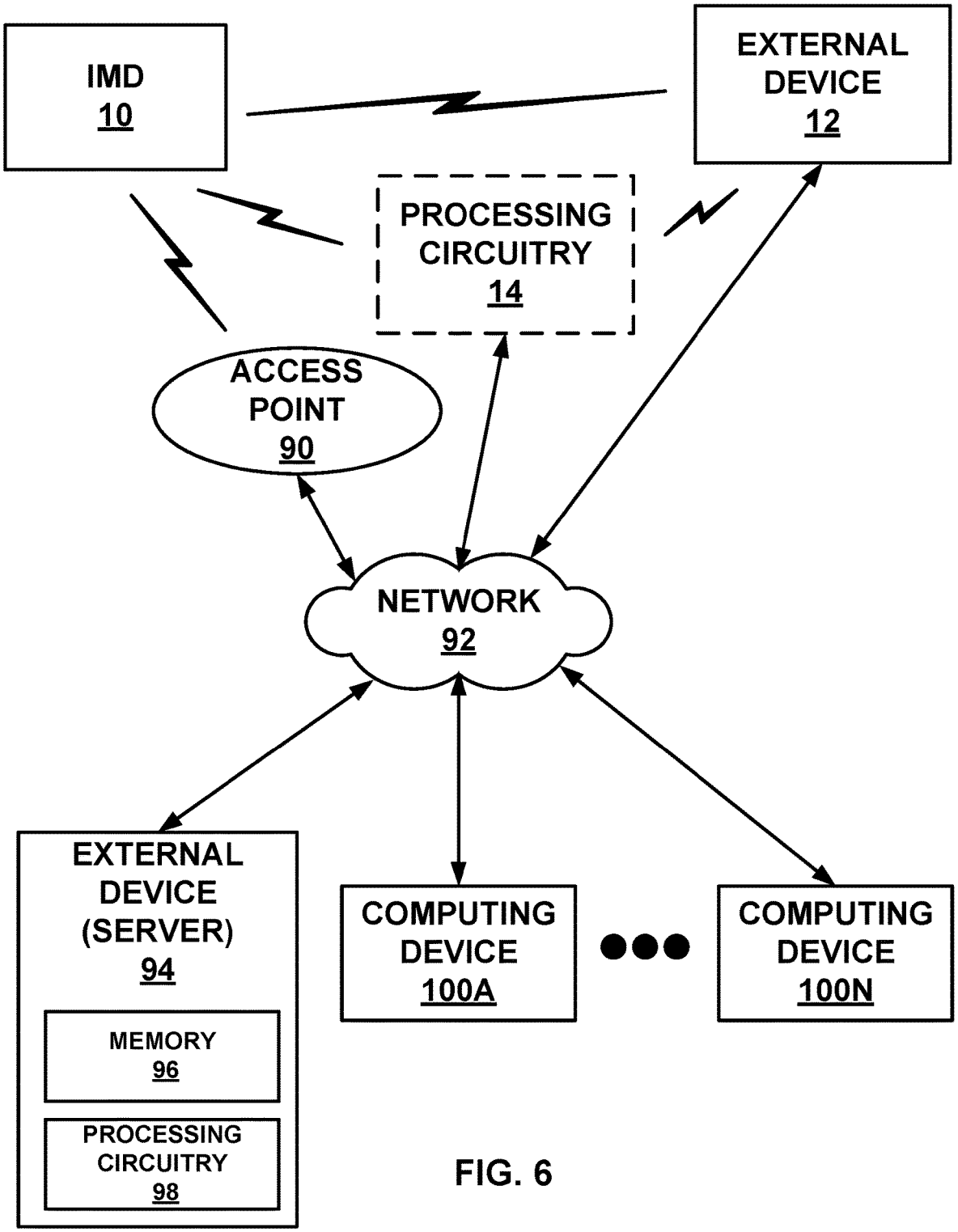
FIG. 6 is a block diagram illustrating an example system that includes an access point, a network, external computing devices, such as a server, and one or more other computing devices, which may be coupled to the IMD of FIGS. 1-4, a sensing device, and an external device via a network, in accordance with one or more techniques described herein.

FIG. 6 is a block diagram illustrating an example system that includes an access point 90, a network 92, external computing devices, such as a server 94, and one or more other computing devices 100A-100N, which may be coupled to IMD 10, external device 12, and processing circuitry 14 via network 92, in accordance with one or more techniques described herein. In this example, IMD 10 may use communication circuitry 54 to communicate with external device 12 via a first wireless connection, and to communication with an access point 90 via a second wireless connection. In the example of FIG. 6, access point 90, external device 12, server 94, and computing devices 100A-100N are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. As discussed above, IMD 10 may be configured to transmit data, such as current values and heart failure statuses, to external device 12. In addition, access point 90 may interrogate IMD 10, such as periodically or in response to a command from the patient or network 92, in order to retrieve current values or heart failure statuses determined by processing circuitry 50 of IMD 10, or other operational or patient data from IMD 10. Access point 90 may then communicate the retrieved data to server 94 via network 92.

In some cases, server 94 may be configured to provide a secure storage site for data that has been collected from IMD 10, and/or external device 12. In some cases, server 94 may assemble data in web pages or other documents for viewing by trained professionals, such as clinicians, via computing devices 100A-100N. One or more aspects of the illustrated system of FIG. 6 may be implemented with general network technology and functionality, which may be similar to that provided by the Medtronic CareLink® Network developed by Medtronic plc, of Dublin, Ireland.

In some examples, one or more of computing devices 100A-100N (e.g., device 100A) may be a tablet or other smart device located with a clinician, by which the clinician may program, receive alerts from, and/or interrogate IMD 10. For example, the clinician may access parameter values (e.g., $StO_2$ values and $SpO_2$ values) associated with patient 4 through device 100A, such as when patient 4 is in in between clinician visits, to check on a heart failure status of patient 4 as desired. In some examples, the clinician may enter instructions for a medical intervention for patient 4 into an app in device 100A, such as based on a heart failure status of patient 4 determined by IMD 10, or based on other patient data known to the clinician. Device 100A then may transmit the instructions for medical intervention to another of computing devices 100A-100N (e.g., device 100B) located with patient 4 or a caregiver of patient 4. For example, such instructions for medical intervention may include an instruction to change a drug dosage, timing, or selection, to schedule a visit with the clinician, or to seek medical attention. In further examples, device 100B may generate an alert to patient 4 based on a heart failure status of patient 4 determined by processing circuitry 14, which may enable patient 4 proactively to seek medical attention prior to receiving instructions for a medical intervention. In this manner, patient 4 may be empowered to take action, as needed, to address his or her heart failure status, which may help improve clinical outcomes for patient 4.

Figure 7:
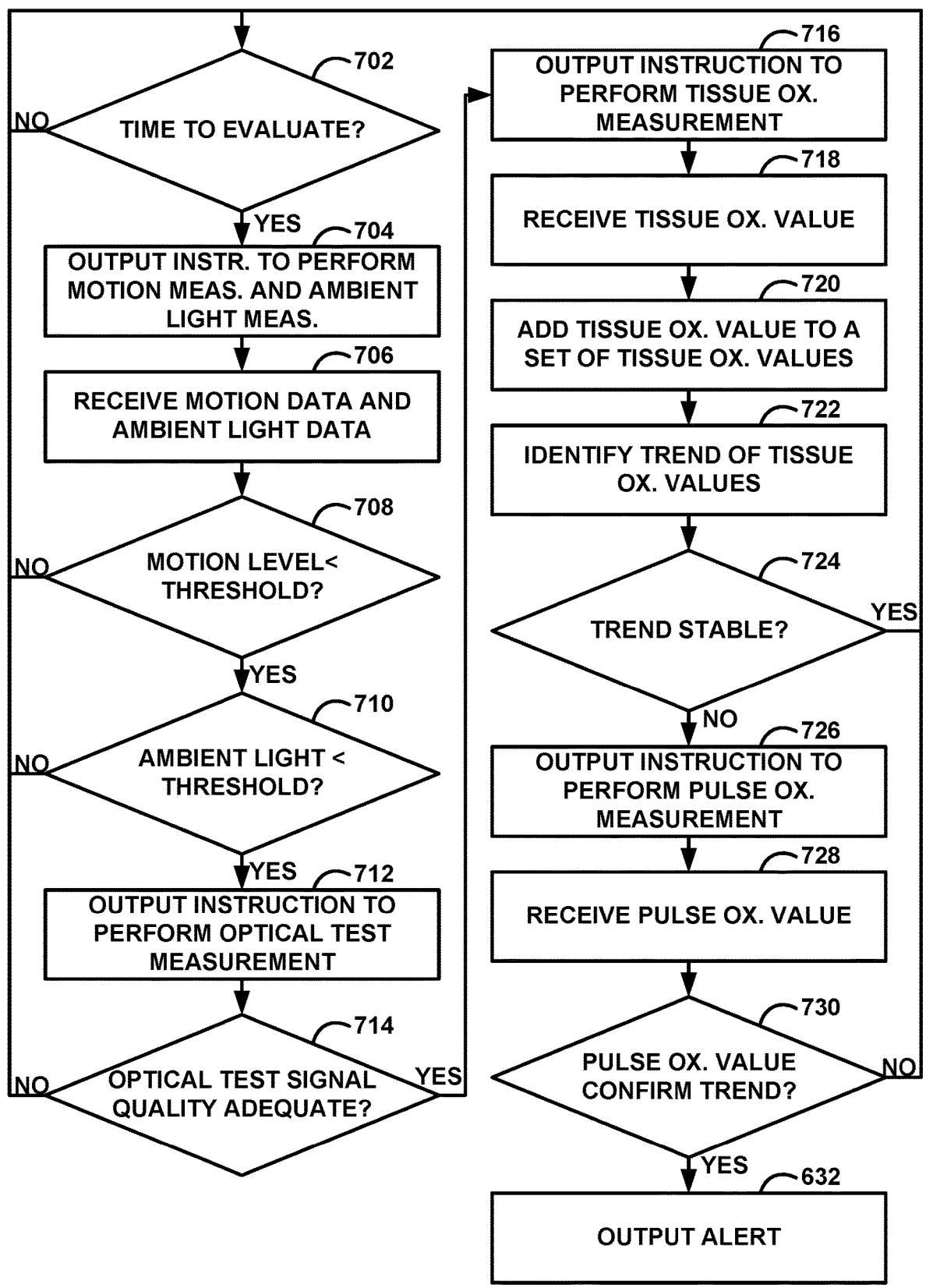
FIG. 7 is a flow diagram illustrating an example operation for performing parameter measurements, in accordance with one or more techniques of this disclosure.

FIG. 7 is a flow diagram illustrating an example operation for performing parameter measurements, in accordance with one or more techniques of this disclosure. For convenience, FIG. 7 is described with respect to IMD 10, external device 12, and processing circuitry 14 of FIGS. 1-4. However, the techniques of FIG. 7 may be performed by different components of IMD 10 or by additional or alternative medical devices.

IMD 10 may, in some examples, be an ICM that measures patient parameters for analysis to identify or monitor one or more patient conditions such as heart failure, sleep apnea, or COPD. In other words, IMD 10 may be implanted in patient 4 to collect data that can be processed to identify a condition causing symptoms that patient 4 is experiencing, and IMD 10 may be implanted in patient 4 to monitor an already-identified patient condition and output an alert if the patient condition is worsening. IMD 10 may be configured to measure a set of parameters including $StO_2$, $SpO_2$, patient motion (e.g., via a motion sensor signal), an amount of ambient light present in tissue, temperature, patient posture, respiration rate, respiration volume, heart rate, heart rate variability, a tissue impedance associated with electrodes 16, or any combination thereof. Data corresponding to at least some of the set of parameters may be analyzed to identify or monitor patient conditions. However, parameter measurements may consume energy, and IMD 10 may be powered by a power source 68 having a finite amount of charge. As such, it may be beneficial to limit an amount of energy used to make parameter measurements, particularly parameter measurements that consume a relatively high amount of power. In some examples, processing circuitry 14 may include processing circuitry 50 of IMD 10, processing circuitry of external device 12, processing circuitry of another device, or any combination thereof.

As illustrated in FIG. 7, processing circuitry 14 determines whether it is time to begin an evaluation of a set of evaluations. The set of evaluations may be performed at an evaluation rate, such that uniform amounts of time separate each consecutive evaluation of the set of evaluations. In this way, processing circuitry 14 is configured to initiate an evaluation when an evaluation is "scheduled." For example, if it is time to perform an hourly, daily, weekly, or monthly evaluation, processing circuitry 14 may start the evaluation.

At block 702, processing circuitry 14 determines whether it is time to perform an evaluation. If it is not time to perform an evaluation ("NO" branch of block 702), processing circuitry 14 again determines whether it is time to begin an evaluation. If it is time to perform an evaluation ("YES" branch of block 702), processing circuitry 14 outputs an instruction to perform a motion level measurement and an ambient light measurement (704). In some examples, processing circuitry 14 outputs the instruction to perform the motion level measurement and the ambient light measurement to IMD 10. Subsequently, processing circuitry 14 receives data corresponding to the motion level measurement and data corresponding to the ambient light measurement (706). In some examples, processing circuitry 14 determines, based on the data corresponding to the motion level measurement, a motion level associated with patient 4. Additionally, in some examples, processing circuitry 14 determines, based on data corresponding to the ambient light measurement, an amount of ambient light present in at least a portion of the tissue of patient 4. In some examples, the data corresponding to the motion level measurement is generated by a motion sensor of IMD 10 and the data corresponding to the ambient light measurement is generated by light detectors 40 of IMD 10.

At block 708, processing circuitry 14 determines whether the motion level derived from the motion level measurement is lower than a threshold motion level. If the motion level is not lower than the threshold motion level ("NO" branch of block 708), the example operation returns to block 702 and the evaluation is complete. In other words, if the motion level is not lower than the threshold motion level, processing circuitry 14 may terminate the evaluation and initiate another evaluation after a period of time, when it is time to perform another evaluation. If the motion level is indeed lower than the threshold motion level ("YES" branch of block 708), processing circuitry 14 proceeds to determine if the amount of ambient light derived from the ambient light measurement is lower than a threshold amount of ambient light (710).

If the amount of ambient light is not lower than the threshold amount of ambient light ("NO" branch of block 710), the example operation returns to block 702 and the evaluation is complete. In other words, if the amount of ambient light is not lower than the threshold amount of ambient light, processing circuitry 14 may terminate the evaluation and initiate another evaluation after a period of time, when it is time to perform another evaluation. If the amount of ambient light is indeed lower than the threshold amount of ambient light ("YES" branch of block 710), processing circuitry 14 outputs an instruction to perform an optical test measurement (712). In some examples, processing circuitry 14 outputs the instruction to perform the optical test measurement to IMD 10, causing IMD 10 to perform the optical test measurement to obtain an optical test signal. Subsequently, IMD 10 may output the optical test signal to processing circuitry 14 for analysis.

In some examples, the threshold amount of ambient light represents a first threshold amount of ambient light. If the amount of ambient light is less than the first threshold amount of ambient light ("YES" branch of block 710), in some cases, processing circuitry 14 may determine whether the amount of ambient light is less than a second threshold amount of ambient light (not illustrated in FIG. 7). If the amount of ambient light is less than the second threshold amount of ambient light, the example operation may proceed to block 712 and processing circuitry 14 outputs the instruction to perform the optical test measurement to IMD 10. If the amount of ambient light is not less than the second threshold amount of ambient light, processing circuitry 14 outputs the instruction to perform the optical test measurement to IMD 10 along with an instruction to subtract an ambient light noise component from data corresponding to a respective $StO_2$ measurement. In this way, if the amount of ambient light is below the first threshold amount of ambient light and greater than or equal to the second threshold amount of ambient light, it may still be possible to perform a sufficient $StO_2$ measurement if the ambient light noise component is subtracted or otherwise eliminated from the data corresponding to the $StO_2$ measurement.

In some examples, the optical test measurement includes an activation of the optical sensor (e.g., light emitter(s) 38 and light detectors 40) of IMD 10. In some examples, the optical test signal resulting from the optical test measurement may include a sequence of datapoints, the sequence having a duration between one second and ten seconds. Additionally, the sequence may include a set of frequency components ranging between 4 Hertz (Hz) and 55 Hz. At block 714, processing circuitry 14 determines whether the optical test signal quality is adequate. For example, processing circuitry 14 may analyze the set of frequency components of the optical test signal to determine whether the optical sensor of IMD 10 is presently capable of generating high-quality optical data. If processing circuitry 14 determines that the optical test signal quality is not adequate ("NO" branch of block 714), the example operation returns to block 702 and the evaluation is complete. In other words, if the optical test signal quality is not adequate, processing circuitry 14 may terminate the evaluation and initiate another evaluation after a period of time, when it is time to perform another evaluation. If processing circuitry 14 determines that the optical test signal quality is adequate ("YES"

branch of block 714), processing circuitry 14 is configured to output an instruction to perform an $StO_2$ measurement (716).

Processing circuitry 14 may, in some cases, output the instruction to perform the $StO_2$ measurement to IMD 10. $StO_2$ measurements may consume significantly more power from power source 68 of IMD 10 than ambient light measurements, motion level measurements, posture measurements, and optical test measurements. In fact, a single $StO_2$ measurement may consume more energy than a combination of the motion level measurement, the ambient light measurement, the posture measurement, and the optical test measurement used by processing circuitry 14 to determine whether to output the instruction to perform the $StO_2$ measurement. As such, although the motion level measurement, the ambient light measurement, the posture measurement, and the optical test measurement consume energy, it may be beneficial to perform such measurements in order to avoid performing an $StO_2$ measurement potentially producing a low-quality $StO_2$ value. In some examples, IMD 10 may continue to monitor motion, posture, and ambient light during the $StO_2$ measurement to verify that these parameters remain relatively constant during the $StO_2$ measurement. If any one or more of motion, posture and ambient light deviate from acceptable values relative to one or more thresholds during the $StO_2$ measurement, processing circuitry 14 may output an instruction to abort the $StO_2$ measurement.

Processing circuitry 14 may receive an $StO_2$ value (718) corresponding to the $StO_2$ measurement. Subsequently, processing circuitry 14 adds the $StO_2$ value to a set of $StO_2$ values (720), where each $StO_2$ value corresponds to a respective $StO_2$ measurement. Based on the set of $StO_2$ values, processing circuitry 14 is configured to identify a trend of $StO_2$ values (722). In some examples, to determine the trend of $StO_2$ values, processing circuitry 14 is configured to plot each $StO_2$ value of the set of $StO_2$ values as a function of time and determine whether the set of $StO_2$ values are increasing, decreasing, or generally remaining constant over a period of time. Additionally in some examples, processing circuitry 14 is configured to identify a rate in which $StO_2$ values are changing, and also determine whether $StO_2$ values exceed or fall below $StO_2$ value thresholds.

At block 724, processing circuitry 14 is configured to determine whether the trend of $StO_2$ values is stable. In some examples, processing circuitry 14 determines that the trend of $StO_2$ values is not stable if the set of $StO_2$ values decrease over a period of time. Such a decrease of $StO_2$ values may indicate that a patient condition such as heart failure is worsening. Alternatively, in some examples, processing circuitry 14 determines that the trend of $StO_2$ values is stable if the set of $StO_2$ values remains relatively constant over a period of time. If processing circuitry 14 determines that the trend of $StO_2$ values is stable ("YES" branch of block 724), the example operation returns to block 702. Subsequently, processing circuitry 14 may initiate another evaluation after a period of time, when it is time to perform another evaluation. If processing circuitry 14 determines that the trend of $StO_2$ values is not stable ("NO" branch of block 724), processing circuitry 14 may output an instruction to perform a pulse oximetry ($SpO_2$) measurement (726). In some examples, processing circuitry 14 outputs the instruction to perform the $SpO_2$ measurement to IMD 10. In other examples, processing circuitry 14 outputs the instruction to perform the $SpO_2$ measurement to another device configured for measuring $SpO_2$. In some examples, processing circuitry 14 outputs a prompt to an external device, and the external device displays the prompt instructing a user to perform an external $SpO_2$ measurement. In examples where processing circuitry 14 outputs the instruction to perform the $SpO_2$ measurement to IMD 10, the $SpO_2$ measurement may consume more energy from power source 68 than an $StO_2$ measurement. As such, it may be beneficial to refrain from taking $SpO_2$ measurement unless processing circuitry 14 determines that the trend of $StO_2$ values is not stable.

$StO_2$ may, in some cases represent a weighted average of $SaO_2$ and $SvO_2$, where $SvO_2$ is more heavily weighted than $SaO_2$. $SpO_2$ may be an approximation of $SaO_2$ alone. In this way, an $SpO_2$ measurement may confirm whether the trend of $StO_2$ values is not stable due to an $SaO_2$ instability or whether the trend of $StO_2$ values is not stable due to an $SvO_2$ instability. Processing circuitry 14 receives an $SpO_2$ value (728) corresponding to the $SpO_2$ measurement. Subsequently, processing circuitry 14 determines whether the $SpO_2$ value confirms the trend of $StO_2$ values (730). In other words, if processing circuitry 14 determines, based on the $SpO_2$ value, that the trend of $StO_2$ values is unstable due to $SaO_2$, then processing circuitry 14 confirms the trend. Alternatively, in some examples, if processing circuitry 14 determines, based on the $SpO_2$ value, that the trend of $StO_2$ values is unstable due to a parameter other than $SaO_2$, then processing circuitry 14 does not confirm the trend. If the $SpO_2$ value does not confirm the trend of $StO_2$ values ("NO" branch of block 730), the example operation returns to block 702. Subsequently, processing circuitry 14 may initiate another evaluation after a period of time, when it is time to perform another evaluation. If the $SpO_2$ value confirms the trend of $StO_2$ values ("YES" branch of block 730), processing circuitry 14 outputs an alert (732).

In some examples, processing circuitry 14 outputs the alert to any combination of external device 12, external server 98, or computing device 100, the alert including information that a patient condition is worsening. In other examples, processing circuitry 14 outputs the alert to another device not pictured in FIGS. 1-4.

Figure 8:
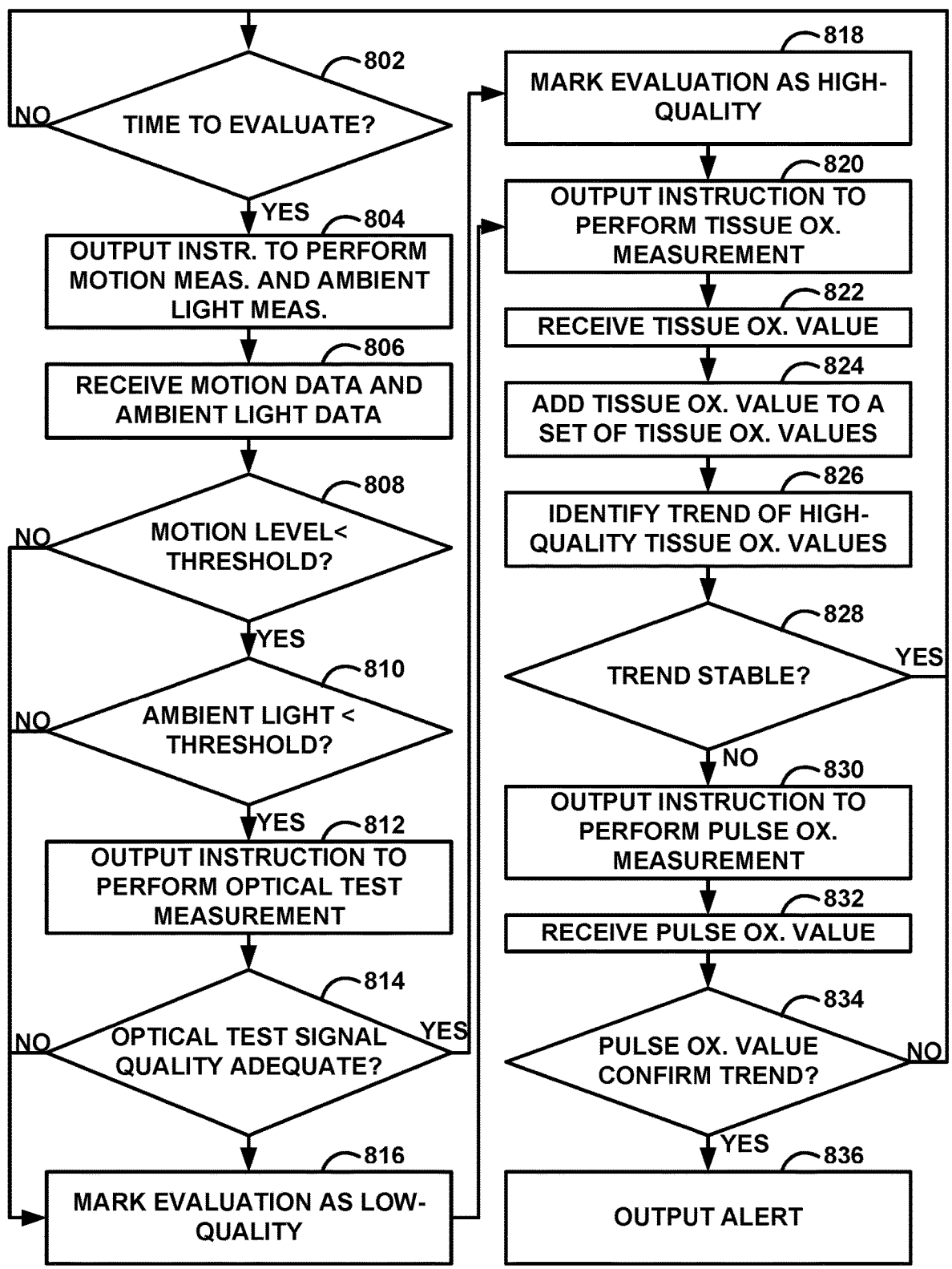
FIG. 8 is a flow diagram illustrating another example operation for performing parameter measurements, in accordance with one or more techniques of this disclosure.

FIG. 8 is a flow diagram illustrating another example operation for performing parameter measurements, in accordance with one or more techniques of this disclosure. For convenience, FIG. 8 is described with respect to IMD 10, external device 12, and processing circuitry 14 of FIGS. 1-4. However, the techniques of FIG. 8 may be performed by different components of IMD 10 or by additional or alternative medical devices.

IMD 10 may, in some examples, be an ICM that measures patient parameters for analysis to identify or monitor one or more patient conditions such as heart failure, sleep apnea, or COPD. In other words, IMD 10 may be implanted in patient 4 to collect data that can be processed to identify a condition causing symptoms that patient 4 is experiencing, and IMD 10 may be implanted in patient 4 to monitor an already-identified patient condition and output an alert if the patient condition is worsening. IMD 10 may be configured to measure a set of parameters including $StO_2$, $SpO_2$, patient motion (e.g., via a motion sensor signal), an amount of ambient light present in tissue, temperature, patient posture, respiration rate, respiration volume, heart rate, heart rate variability, a tissue impedance associated with electrodes 16, or any combination thereof. Data corresponding to at least some of the set of parameters may be analyzed to identify or monitor patient conditions. However, some parameter measurements may be noisy, or low-quality for another reason. As such, in some examples, it may be beneficial to identify parameter measurements that may be low-quality, so that these low-quality parameter measurements may be excluded when parameter measurements are analyzed to identify or monitor a patient condition. In some examples, processing circuitry 14 may include processing circuitry 50 of IMD 10, processing circuitry of external device 12, processing circuitry of another device, or any combination thereof.

As illustrated in FIG. 8, Processing circuitry 14 determines whether it is time to begin an evaluation of a set of evaluations. The set of evaluations may be performed at an evaluation rate, such that uniform amounts of time separate each consecutive evaluation of the set of evaluations. In this way, processing circuitry 14 is configured to initiate an evaluation when an evaluation is "scheduled." For example, if it is time to perform an hourly, daily, weekly, or monthly evaluation, processing circuitry 14 may start the evaluation.

At block 802, processing circuitry 14 determines whether it is time to perform an evaluation. If it is not time to perform an evaluation ("NO" branch of block 802), the processing circuitry 14 again determines whether it is time to begin an evaluation. If it is time to perform an evaluation ("YES" branch of block 802), processing circuitry 14 outputs an instruction to perform a motion level measurement and an ambient light measurement (804). In some examples, processing circuitry 14 outputs the instruction to perform the motion level measurement and the ambient light measurement to IMD 10. Subsequently, processing circuitry 14 receives data corresponding to the motion level measurement and data corresponding to the ambient light measurement (806). In some examples, processing circuitry 14 determines, based on the data corresponding to the motion level measurement, a motion level associated with patient 4. Additionally, in some examples, processing circuitry 14 determines, based on data corresponding to the ambient light measurement, an amount of ambient light present in at least a portion of the tissue of patient 4. In some examples, the data corresponding to the motion level measurement is generated by a motion sensor of IMD 10 and the data corresponding to the ambient light measurement is generated by light detectors 40 of IMD 10.

At block 808, processing circuitry 14 determines whether the motion level derived from the motion level measurement is lower than a threshold motion level. If the motion level is not lower than the threshold motion level ("NO" branch of block 808), processing circuitry 14 marks the evaluation as low-quality (816). In other words, high motion levels may interfere with a potential $StO_2$ measurement by introducing noise into the $StO_2$ measurement, and processing circuitry 14 may identify data associated with $StO_2$ measurements performed under such high-motion conditions as potentially being of low-quality. If the motion level is indeed lower than the threshold motion level ("YES" branch of block 808), processing circuitry 14 proceeds to determine if the amount of ambient light derived from the ambient light measurement is lower than a threshold amount of ambient light (810).

If the amount of ambient light is not lower than the threshold amount of ambient light ("NO" branch of block 810), processing circuitry 14 marks the evaluation as low-quality (816). In other words, high amounts of ambient light may interfere with a potential $StO_2$ measurement by introducing noise into the $StO_2$ measurement, and processing circuitry 14 may identify data associated with $StO_2$ measurements performed under such high-ambient light conditions as potentially being of low-quality. If the amount of ambient light is indeed lower than the threshold amount of ambient light ("YES" branch of block 810), processing circuitry 14 outputs an instruction to perform an optical test measurement (812). In some examples, processing circuitry 14 outputs the instruction to perform the optical test measurement to IMD 10, causing IMD 10 to perform the optical test measurement to obtain an optical test signal. Subsequently, IMD 10 may output the optical test signal to processing circuitry 14 for analysis.

In some examples, the threshold amount of ambient light represents a first threshold amount of ambient light. If the amount of ambient light is less than the first threshold amount of ambient light ("YES" branch of block 810), in some cases, processing circuitry may determine whether the amount of ambient light is less than a second threshold amount of ambient light (not illustrated in FIG. 8). If the amount of ambient light is less than the second threshold amount of ambient light, the example operation may proceed to block 812 and processing circuitry 14 outputs the instruction to perform the optical test measurement to IMD 10. If the amount of ambient light is not less than the second threshold amount of ambient light, processing circuitry 14 outputs the instruction to perform the optical test measurement to IMD 10 along with an instruction to subtract an ambient light noise component from data corresponding to a respective $StO_2$ measurement. In this way, if the amount of ambient light is below the first threshold amount of ambient light and greater than or equal to the second threshold amount of ambient light, it may still be possible to perform a "high quality" $StO_2$ measurement if the ambient light noise component is subtracted or otherwise eliminated from the data corresponding to the $StO_2$ measurement.

In some examples, the optical test measurement includes an activation of the optical sensor (e.g., light emitter(s) 38 and light detectors 40) of IMD 10. In some examples, the optical test signal resulting from the optical test measurement may include a sequence of data points, the sequence having a duration between one second and ten seconds. Additionally, the sequence may include a set of frequency components ranging between 4 Hertz (Hz) and 55 Hz. At block 814, processing circuitry 14 determines whether the optical test signal quality is adequate. For example, processing circuitry 14 may analyze the set of frequency components of the optical test signal to determine whether the optical sensor of IMD 10 is presently capable of generating high-quality optical data. If processing circuitry 14 determines that the optical test signal quality is not adequate ("NO" branch of block 814), processing circuitry 14 marks the evaluation as low-quality (816). In other words, if the optical test signal is not adequate, a potential $StO_2$ measurement may produce a low-quality $StO_2$ value. If processing circuitry 14 determines that the optical test signal quality is adequate ("YES" branch of block 814), processing circuitry 14 is configured to mark the evaluation as high-quality (818).

In both cases where processing circuitry 14 marks the evaluation as low-quality and where processing circuitry 14 marks the evaluation as high-quality, processing circuitry 14 outputs an instruction to perform an $StO_2$ measurement (820). In some examples, processing circuitry 14 outputs the instruction to perform the $StO_2$ measurement to IMD 10. Subsequently, processing circuitry 14 receives data indicative of an $StO_2$ value (822) and adds the $StO_2$ value to a set of $StO_2$ values (824). Processing circuitry 14 is configured to identify a trend of high-quality $StO_2$ values (826). As such, processing circuitry 14 may, in some cases, identify high-quality $StO_2$ values of the set of $StO_2$ values. High quality $StO_2$ values correspond to $StO_2$ measurements that are performed following an evaluation marked as high-quality by processing circuitry 14. In other words, processing circuitry 14 may exclude low-quality $StO_2$ values while identifying a trend in $StO_2$ values. In this way, the trend identified by processing circuitry 14 may not be compromised with data points that are inadequate due to noise of non-uniform measurement circumstances.

At block 828, processing circuitry 14 is configured to determine whether the trend of high-quality $StO_2$ values is stable. In some examples, processing circuitry 14 determines that the trend of high-quality $StO_2$ values is not stable if the high-quality $StO_2$ values decrease over a period of time. Such a decrease of $StO_2$ values may indicate that a patient condition such as heart failure is worsening. Alternatively, in some examples, processing circuitry 14 determines that the trend of $StO_2$ values is stable if the high-quality $StO_2$ values remain relatively constant over a period of time. If processing circuitry 14 determines that the trend of high-quality $StO_2$ values is stable ("YES" branch of block 828), the example operation returns to block 802. Subsequently, processing circuitry 14 may initiate another evaluation after a period of time, when it is time to perform another evaluation. If processing circuitry 14 determines that the trend of $StO_2$ values is not stable ("NO" branch of block 828), processing circuitry 14 may output an instruction to perform a pulse oximetry ($SpO_2$) measurement (830). In some examples, processing circuitry 14 outputs the instruction to perform the $SpO_2$ measurement to IMD 10. In other examples, processing circuitry 14 outputs the instruction to perform the $SpO_2$ measurement to another device configured for measuring $SpO_2$. In examples where processing circuitry 14 outputs the instruction to perform the $SpO_2$ measurement to IMD 10, the $SpO_2$ measurement may consume more energy from power source 68 than an $StO_2$ measurement. As such, it may be beneficial to refrain from taking $SpO_2$ measurement unless processing circuitry 14 determines that the trend of $StO_2$ values is not stable.

Processing circuitry 14 receives an $SpO_2$ value (832) corresponding to the $SpO_2$ measurement. Subsequently, processing circuitry 14 determines whether the $SpO_2$ value confirms the trend of $StO_2$ values (834). In other words, if processing circuitry 14 determines, based on the $SpO_2$ value, that the trend of $StO_2$ values is unstable due to $SaO_2$, then processing circuitry 14 confirms the trend. Alternatively, in some examples, if processing circuitry 14 determines, based on the $SpO_2$ value, that the trend of $StO_2$ values is unstable due to a parameter other than $SaO_2$, then processing circuitry 14 does not confirm the trend. If the $SpO_2$ value does not confirm the trend of $StO_2$ values ("NO" branch of block 834), the example operation returns to block 802. Subsequently, processing circuitry 14 may initiate another evaluation after a period of time, when it is time to perform another evaluation. If the $SpO_2$ value confirms the trend of $StO_2$ values ("YES" branch of block 834), processing circuitry 14 outputs an alert (836).

In some examples, processing circuitry 14 outputs the alert to any combination of external device 12, external server 98, or computing device 100, the alert including information that a patient condition is worsening. In other examples, processing circuitry 14 outputs the alert to another device not pictured in FIGS. 1-4.

Figure 9:
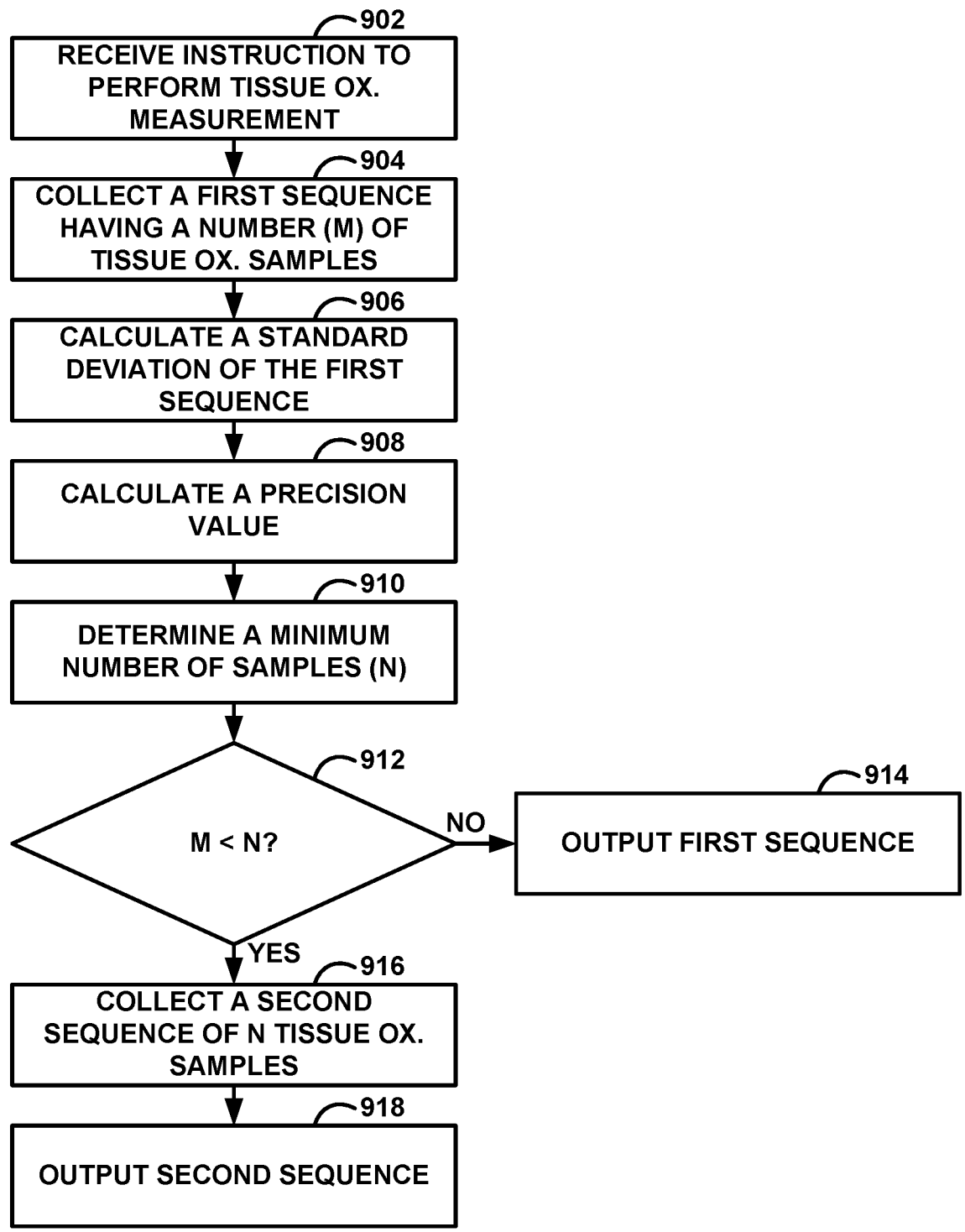
FIG. 9 is a flow diagram illustrating an example operation for performing a tissue oxygen saturation measurement using the implantable medical device of FIGS. 1-4, in accordance with one or more techniques described herein.

FIG. 9 is a flow diagram illustrating an example operation for performing a tissue oxygen saturation measurement using IMD 10, in accordance with one or more techniques described herein. For convenience, FIG. 9 is described with respect to IMD 10 of FIGS. 1-4. However, the techniques of FIG. 9 may be performed by different components of IMD 10 or by additional or alternative medical devices.

When IMD 10 performs an $StO_2$ measurement, it may be beneficial to collect enough $StO_2$ samples to ensure that the $StO_2$ value that is determined based on the $StO_2$ samples is adequate (e.g., a greater number of $StO_2$ samples collected during an $StO_2$ measurement may improve a quality/accuracy/noise level of the $StO_2$ value). Additionally, in some examples, it may be beneficial to limit a number of $StO_2$ samples collected during an $StO_2$ measurement in order to conserve a charge level of the power source 68 which provides power to the components of IMD 10 (e.g., a greater number of $StO_2$ samples causes the optical sensor to consume a greater amount of electrical current). IMD 10 may be configured to balance the number of $StO_2$ samples that IMD 10 collects during an $StO_2$ measurement by determining a minimum number of $StO_2$ samples for producing an adequate quality $StO_2$ value.

As illustrated in FIG. 9, IMD 10 may receive an instruction to perform an $StO_2$ measurement (902). IMD 10 may receive the instruction from external device 12, processing circuitry 14, or another device not illustrated in FIGS. 1-4. In some examples, IMD 10 receives the instruction from processing circuitry 50 of IMD 10 (which may, in some cases, be a part of processing circuitry 14). In other examples, IMD 10 receives the instruction from another device via antenna 26 and communication circuitry 54. After receiving the instruction, IMD 10 collects a first sequence of $StO_2$ samples, where the sequence includes a number (M) of $StO_2$ samples (904). In some examples, the first sequence of $StO_2$ samples has a sampling frequency between 2 Hz and 10 Hz. Additionally, in some examples, a duration of the sequence is between 5 seconds and 15 seconds. Each sample of the first sequence of $StO_2$ samples may represent a sample $StO_2$ value.

Processing circuitry 50 of IMD 10 may calculate a standard deviation of the first sequence of $StO_2$ samples (906). Based on the standard deviation, processing circuitry 50 calculates a precision value (908) associated with the first sequence of $StO_2$ samples. A higher standard deviation may be indicative of a higher precision value and a lower standard deviation may be indicative of a lower precision value. Based on the precision value, processing circuitry 50 may determine a minimum number (N) of $StO_2$ samples (910) required for an adequate $StO_2$ measurement. Processing circuitry 50 may store M to be used as N in a subsequent iteration of the example operation of FIG. 9.

At block 912, processing circuitry 50 determines if the number of samples (M) included in the first sequence of $StO_2$ samples is less than the minimum number of samples (N) required for an adequate $StO_2$ measurement. If M is not less than N ("NO" branch of block 912), IMD 10 may complete the $StO_2$ measurement and output the first sequence of $StO_2$ samples (914). If M is indeed less than N ("YES" branch of block 912), IMD 10 may collect a second sequence of N $StO_2$ samples (916). In some examples, IMD 10 may subtract M from N to obtain a sample difference value and store the sample difference value in memory 56. Subsequently, IMD 10 may complete the $StO_2$ measurement and output the second sequence of $StO_2$ samples (918). In this way, IMD 10 may ensure that an $StO_2$ measurement includes at least N samples, thus improving a quality of $StO_2$ measurements by collecting an adequate amount of data during each $StO_2$ measurement.

Figure 10:
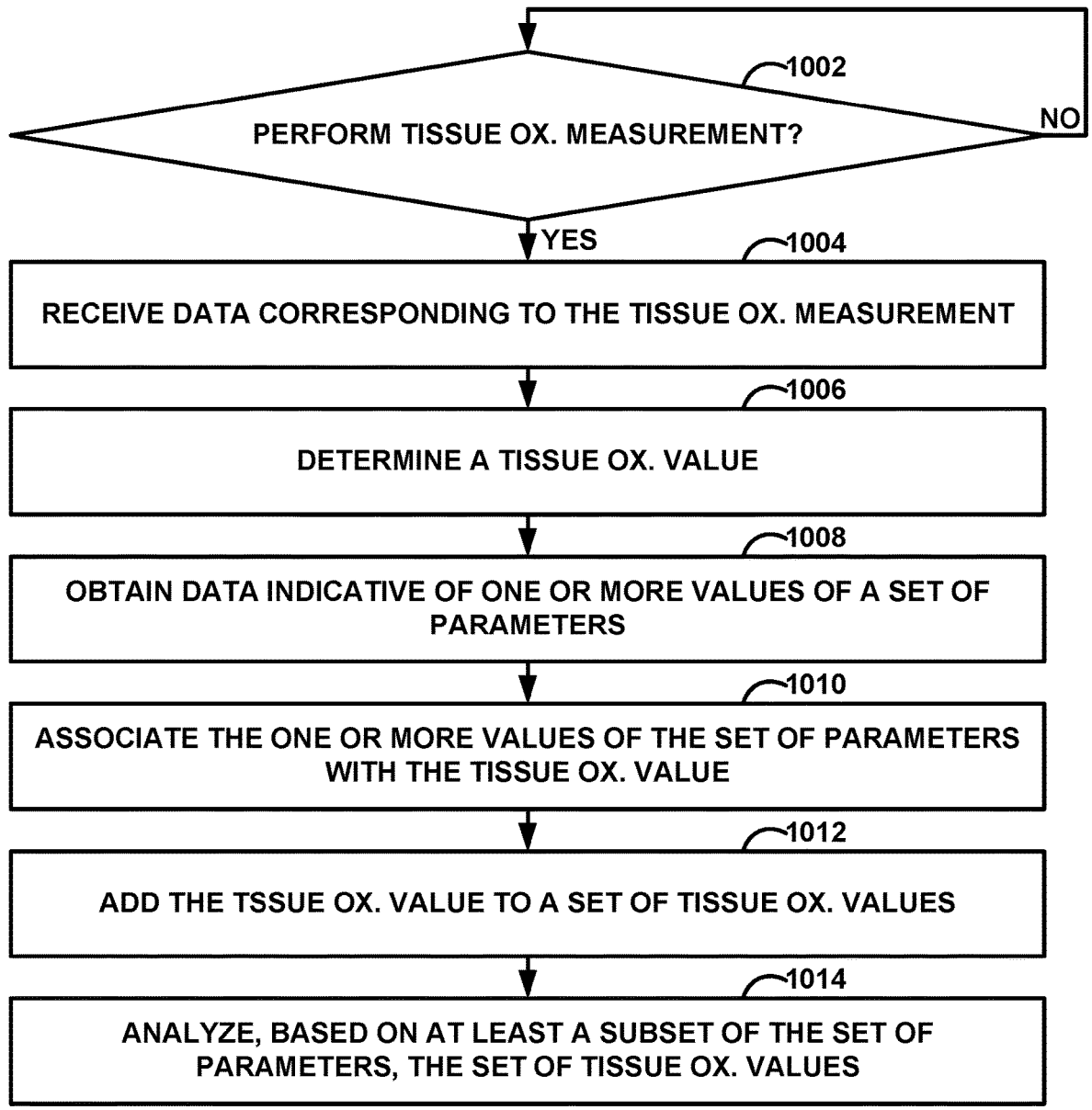
FIG. 10 is a flow diagram illustrating an example operation for analyzing tissue oxygen saturation values, in accordance with one or more techniques of this disclosure.

FIG. 10 is a flow diagram illustrating an example operation for analyzing tissue oxygen saturation values, in accordance with one or more techniques of this disclosure. For convenience, FIG. 10 is described with respect to IMD 10, external device 12, and processing circuitry 14 of FIGS. 1-4.

However, the techniques of FIG. 10 may be performed by different components of IMD 10 or by additional or alternative medical devices.

In the example operation of FIG. 10, processing circuitry 14 determines whether to control IMD 10 to perform an $StO_2$ measurement (1002). In some examples, processing circuitry 14 may determine whether to control IMD 10 to perform the $StO_2$ measurement based on an evaluation performed by processing circuitry 14. The evaluation, in some cases, may include an analysis of whether one or more parameters meet respective threshold values or respective ranges of threshold values. In some examples, processing circuitry 14 determines to control IMD 10 to perform $StO_2$ measurements at a measurement frequency (e.g., one measurement per hour, one measurement per day, or any other valid frequency). If processing circuitry determines not to control IMD 10 to perform the $StO_2$ measurement ("NO" branch of block 912), the example operation returns to block 1002 and processing circuitry 14 reevaluates whether to control IMD 10 to perform a $StO_2$ measurement.

If processing circuitry 14 determines to control IMD 10 to perform the $StO_2$ measurement ("YES" branch of block 912), processing circuitry 14 receives, from IMD 10, data corresponding to the $StO_2$ measurement (1004) and determines, based on the data corresponding to the $StO_2$ measurement, a tissue oxygen saturation value (1006). In some examples, if processing circuitry 14 determines to control IMD 10 to perform the $StO_2$ measurement, processing circuitry 14 may determine to classify the measurement as either a high-quality measurement or a low-quality measurement based on an evaluation performed by processing circuitry 14. Processing circuitry 14 may elect to exclude low-quality measurements from analysis. Processing circuitry 14 may obtain data indicative of one or more values of a set of parameters (1008). In some examples, the one or more values are measured by IMD 10 within a time window corresponding to a time in which the $StO_2$ measurement is performed. In this way, the one or more values may be reflective of present conditions when the $StO_2$ measurement is performed by IMD 10. In some examples, the set of parameters may include any combination of an amount of ambient light present in target tissue of patient 4, an optical sensor test signal, a temperature of the target tissue, a posture of patient 4 (e.g., a sitting position, a standing position, a prone position, or a supine position), a respiration rate, a respiration volume, a heart rate, a heart rate variability, and a subcutaneous tissue impedance. By obtaining the data indicative of the one or more values of the set of parameters, processing circuitry 14 may be configured to classify the tissue oxygen saturation value based on the set of parameters.

For example, processing circuitry 14 may associate the one or more values of the set of parameters with the tissue oxygen saturation value (1010) and add the tissue oxygen saturation value to a set of tissue oxygen saturation values (1012). In some cases, each tissue oxygen saturation value of the set of tissue oxygen saturation values is associated with a respective $StO_2$ measurement, the respective measurement corresponding to a respective one or more values of the set of parameters. In this way, the values—which may be indicative of conditions at the time the respective $StO_2$ measurement is performed by IMD 10—may enable processing circuitry 14 to perform one or more custom analyses of the set of tissue oxygen saturation values. For example, processing circuitry 14 analyzes, based on at least a subset of the set of parameters, the set of tissue oxygen saturation values (1014).

In some cases, processing circuitry 14 may determine, in the set of tissue oxygen saturation values, a first subset of tissue oxygen saturation values corresponding to $StO_2$ measurements that are performed while patient 4 is lying in a supine position. Additionally, in some cases, processing circuitry 14 may determine, in the set of tissue oxygen saturation values, a second subset of tissue oxygen saturation values corresponding to $StO_2$ measurements that are performed while patient 4 is lying in a prone position. In this way, processing circuitry may be configured to compare tissue oxygen data corresponding to when patient 4 is lying supine and tissue oxygen data corresponding to when patient 4 is lying prone. The analysis is not limited to a supine/prone comparison. Processing circuitry 14 may split the set of tissue oxygen saturation values into any number of subsets and perform an analysis based on any of the set of parameters.

Figure 11:
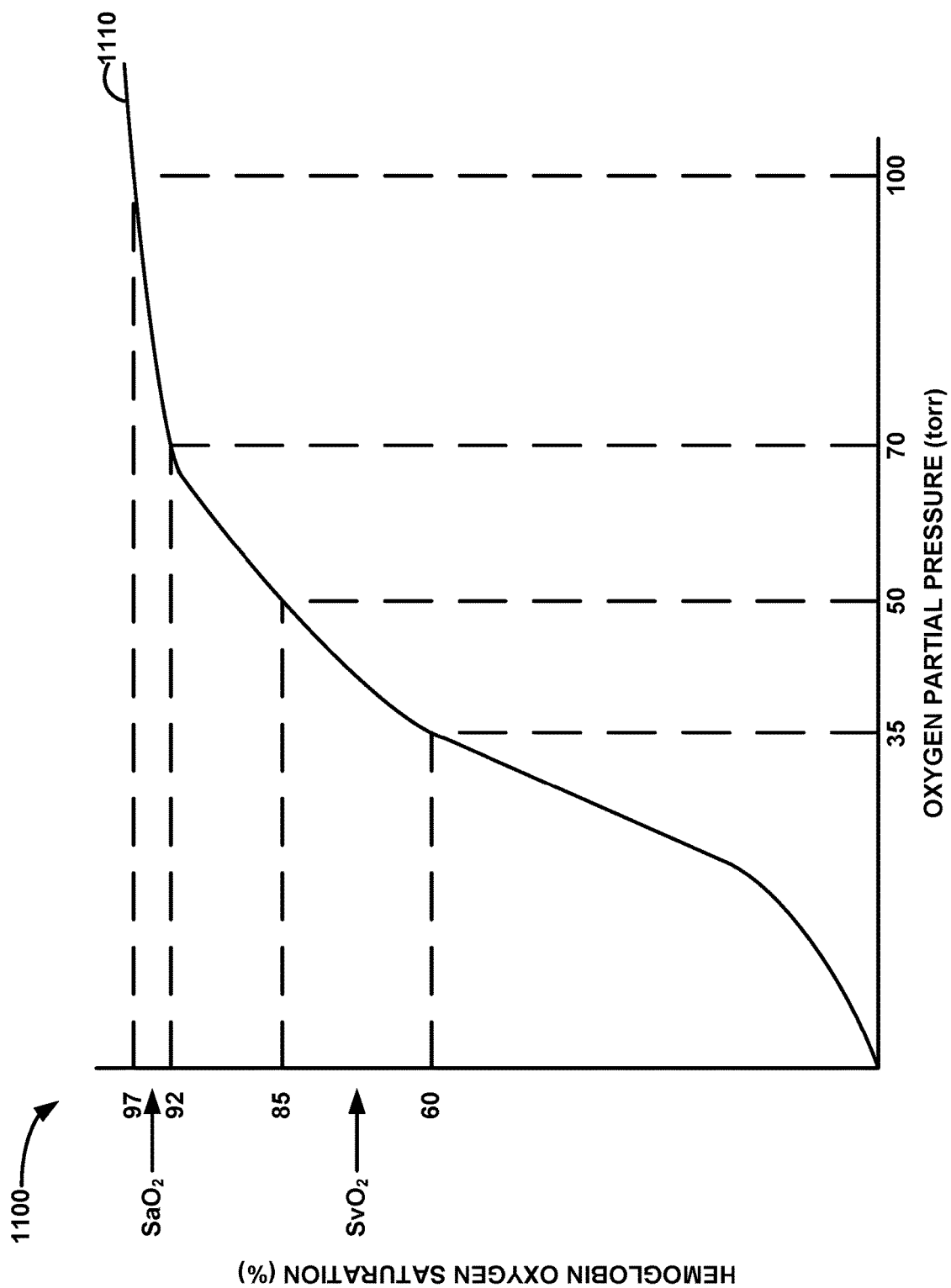
FIG. 11 is a graph illustrating a hemoglobin saturation/oxygen partial pressure plot, in accordance with one or more techniques of this disclosure.

FIG. 11 is a graph illustrating a hemoglobin oxygen saturation/oxygen partial pressure plot 1100, in accordance with one or more techniques of this disclosure. For example, FIG. 11 includes a plot line 1110 which tracks a relationship between a hemoglobin oxygen saturation percentage and a partial pressure of oxygen. In some examples, the partial pressure of oxygen represents a true underlying oxygen delivery capability of whole blood.

As seen in FIG. 11, when hemoglobin oxygen saturation is greater than 90% (e.g., between 92% and 97%), there is a relatively low oxygen saturation sensitivity to the partial pressure of oxygen in solution. In other words, a small change in $SaO_2$ corresponds to a relatively large change in the partial pressure of oxygen. On the contrary, for venous blood, where $SvO_2$ may, in some cases, occupy a range between 60% and 80%, there is a relatively high oxygen saturation sensitivity to the partial pressure of oxygen in solution. In other words, a large change in $SvO_2$ corresponds to a relatively small change in the partial pressure of oxygen. The venous blood partial pressure of oxygen is related to the arterial blood through flow rate and metabolism of the local tissue located within range of the optical sensors of IMD 10. For example, if the arterial blood oxygen saturation, flow, and local metabolism do not change, then venous blood oxygen saturation, flow, and local metabolism may also remain constant.

As such, although $StO_2$ may represent a weighted average of $SaO_2$ and $SvO_2$, if $SaO_2$ remains stable in patient 4, it may be likely that $StO_2$ also remains stable in patient 4 under conditions of substantially constant metabolism and substantially constant cardiac output. Additionally, if $SaO_2$ changes in patient 4, it may be likely that $StO_2$ also changes in patient 4. However, an opposite scenario is not always true. For example, in some cases, if $StO_2$ changes, the change may be caused by a change in blood flow or a change in oxygen metabolism of local tissue—rather than a change in $SaO_2$. It is for this reason, at least partially, that it may be beneficial to perform an $SpO_2$ measurement in response to determining that a trend of $StO_2$ values is unstable. Since an $SpO_2$ value is indicative of $SaO_2$, performing an $SpO_2$ measurement using IMD 10 may confirm if $StO_2$ changes are related to corresponding changes in $SaO_2$, or if the $StO_2$ changes are related to changes in other parameters, such as $SvO_2$, blood flow, or oxygen metabolism of local tissue. Additional parameter measurements, such as impedance measurements and doppler flow measurements may help to further differentiate between blood flow vs local tissue metabolism. Although $SpO_2$ is a good indicator of $SaO_2$, $StO_2$ may also be a good indicator in $SaO_2$. In other words, tracking changes in $StO_2$ values may be useful for tracking changes in $SaO_2$ over a period of time under conditions of substantially constant metabolism and substantially constant cardiac output.

Oxygen metabolism of local tissue may affect $StO_2$. For example, in some cases, muscular tissue may lose the ability to metabolize oxygen. In some such cases, $StO_2$ may increase over a period of time. In other such cases, $StO_2$ may remain constant if local tissue metabolism and blood flow decrease or if $SaO_2$ decreases. For example, in examples where patient 4 has heart failure, cardiac output capacity of patient 4 may decrease and muscle tissue of patient 4 may lose metabolic capability. However, it may be uncommon or even rare for these competing effects to cause no change in $StO_2$.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical device system comprising:
    an optical sensor configured to measure ambient light and a tissue oxygen saturation parameter; and
    processing circuitry configured to perform a plurality of evaluations, wherein, for each of the evaluations, the processing circuitry is configured to:
        determine that the evaluation is prompted, wherein the evaluation is associated with a current measurement of the tissue oxygen saturation parameter;
        control the optical sensor to perform an ambient light measurement associated with the current measurement of the tissue oxygen saturation parameter;
        determine, based on the ambient light measurement, at least one of:
            whether to control the optical sensor to perform the current measurement of the tissue oxygen saturation parameter,
            when to control the optical sensor to perform the current measurement of the tissue oxygen saturation parameter, or
            whether to include the current measurement of the tissue oxygen saturation parameter in a trend of the tissue oxygen saturation parameter; and
        complete the evaluation based on determining at least one of whether to control the optical sensor to perform the current measurement, when to control the optical sensor to perform the current measurement, or whether to include the current measurement in the trend.

2. The medical device system of claim 1, further comprising a motion sensor configured to measure motion of a patient, wherein, for each of the plurality of evaluations, the processing circuitry is further configured to:
    control the motion sensor to perform a motion level measurement associated with the current measurement of the tissue oxygen saturation parameter; and
    determine, based on the ambient light measurement and the motion level measurement, at least one of whether to control the optical sensor to perform the current measurement, when to control the optical sensor to perform the current measurement, or whether to include the current measurement in the trend.

3. The medical device system of claim 2, wherein to determine at least one of whether to control the optical sensor to perform the current measurement, when to control the optical sensor to perform the current measurement, or whether to include the current measurement in the trend, the processing circuitry is configured to:
    receive, from the optical sensor, data corresponding to the ambient light measurement;
    receive, from the motion sensor, data corresponding to the motion level measurement; determine, based on the data corresponding to the motion level measurement, a motion level associated with the patient;
    determine, based on the data corresponding to the ambient light measurement, an amount of ambient light present in target tissue;
    compare the motion level with a threshold motion level; and
    compare the amount of ambient light with a threshold amount of ambient light.

4. The medical device system of claim 3, wherein the optical sensor is further configured to measure an optical sensor test signal, and wherein, for each of the plurality of evaluations, the processing circuitry is further configured to:
    control the optical sensor to perform an optical sensor test measurement associated with the current measurement of the tissue oxygen saturation parameter; and
    determine, based on the ambient light measurement, the motion level measurement, and the optical sensor test measurement, at least one of whether to control the optical sensor to perform the current measurement, when to control the optical sensor to perform the current measurement, or whether to include the current measurement in the trend.

5. The medical device system of claim 4, wherein to determine at least one of whether to control the optical sensor to perform the current measurement, when to control the optical sensor to perform the current measurement, or whether to include the current measurement in the trend, the processing circuitry is further configured to:

receive, from the optical sensor, an optical sensor test signal corresponding to the optical sensor test measurement; and determine, based on the optical sensor test signal, whether an optical sensor test signal quality is adequate.

6. The medical device system of claim 5, wherein the processing circuitry is configured to determine not to control the optical sensor to perform the current measurement of the tissue oxygen saturation parameter if:

the motion level is greater than or equal to the threshold motion level;

the amount of ambient light is greater than or equal to the threshold amount of ambient light; or the optical sensor test signal quality is not adequate, and wherein the processing circuitry is configured to determine to control the optical sensor to perform the current measurement of the tissue oxygen saturation parameter if:

the motion level is less than the threshold motion level;

the amount of ambient light is less than the threshold amount of ambient light; and the optical sensor test signal quality is adequate.

7. The medical device system of claim 5, wherein the processing circuitry is configured to determine not to include the current measurement of the tissue oxygen saturation parameter in the trend of the tissue oxygen saturation parameter if:

the motion level is greater than or equal to the threshold motion level;

the amount of ambient light is greater than or equal to the threshold amount of ambient light; or the optical sensor test signal quality is not adequate, and wherein the processing circuitry is configured to determine to include the current measurement of the tissue oxygen saturation parameter in the trend of the tissue oxygen saturation parameter if:

the motion level is less than the threshold motion level;

the amount of ambient light is less than the threshold amount of ambient light; and the optical sensor test signal quality is adequate.

8. The medical device system of claim 2, further comprising a medical device comprising a set of sensors including the optical sensor, the motion sensor, and one or more electrodes.

9. The medical device system of claim 8, wherein the medical device comprises an implantable medical device (IMD) configured to be implanted outside of a thoracic cavity of the patient.

10. The medical device system of claim 8, wherein if the processing circuitry determines to control the optical sensor to perform the current measurement, the processing circuitry is configured to:

receive, from the optical sensor, data corresponding to the current measurement of the tissue oxygen saturation parameter;

determine, based on the data corresponding to the current measurement of the tissue oxygen saturation parameter, a tissue oxygen saturation value; and classify, based on a set of parameters measured by the set of sensors, the tissue oxygen saturation value.

11. The medical device system of claim 10, wherein to classify the current measurement, the processing circuitry is configured to:

obtain data indicative of one or more values of the set of parameters, wherein the one or more values are measured within a time window associated with a time in which the current measurement is performed;

associate the one or more values of the set of parameters with the tissue oxygen saturation value;

add the tissue oxygen saturation value to a set of tissue oxygen saturation values, wherein each tissue oxygen saturation value of the set of tissue oxygen saturation values is associated with a respective measurement of the tissue oxygen saturation parameter, the respective measurement corresponding to a respective one or more values of the set of parameters; and analyze, based on at least a subset of the set of parameters, the set of tissue oxygen saturation values.

12. The medical device system of claim 10, wherein the set of parameters includes any one or more of an amount of ambient light present in target tissue, an optical sensor test signal, a temperature of the target tissue, a posture of the patient, a respiration rate, a respiration volume, a heart rate, a heart rate variability, a tissue hemoglobin index (THI) value, or a subcutaneous tissue impedance.

13. The medical device system of claim 1, wherein when the processing circuitry determines to control the optical sensor to perform the current measurement of the tissue oxygen saturation parameter, and wherein the processing circuitry is further configured to:

receive, from the optical sensor, data corresponding to the current measurement of the tissue oxygen saturation parameter;

determine, based on the data corresponding to the current measurement of the tissue oxygen saturation parameter, a tissue oxygen saturation value; and add the tissue oxygen saturation value to a set of tissue oxygen saturation values, wherein each tissue oxygen saturation value of the set of tissue oxygen saturation values is associated with a respective measurement of the tissue oxygen saturation parameter.

14. The medical device system of claim 13, wherein the processing circuitry is further configured to:

identify, based on the set of tissue oxygen saturation values, the trend of the tissue oxygen saturation parameter; and determine whether the trend of the tissue oxygen saturation parameter is stable.

15. The medical device system of claim 14, wherein if the processing circuitry determines that the trend of the tissue oxygen saturation parameter is not stable, the processing circuitry is configured to:

control performance of a pulse oximetry measurement associated with the current measurement of the tissue oxygen saturation parameter.

16. The medical device system of claim 15, wherein the processing circuitry is configured to control the optical sensor to perform the pulse oximetry measurement.

17. The medical device system of claim 16, wherein the processing circuitry is configured to:

receive data corresponding to the pulse oximetry measurement;

determine, based on the data corresponding to the pulse oximetry measurement, a pulse oxygen saturation value;

compare the pulse oxygen saturation value with a threshold pulse oxygen saturation value; and based on the comparison between the pulse oxygen saturation value and the threshold pulse oxygen saturation value, determine whether to output an alert.

18. The medical device system of claim 1, wherein to determine when to control the optical sensor to perform the current measurement of the tissue oxygen saturation parameter, the processing circuitry is configured to:
determine whether to delay the current measurement of the tissue oxygen saturation parameter by an amount of time.

19. A method comprising:
measuring, using an optical sensor of a medical device system, ambient light and a tissue oxygen saturation parameter;
performing, using processing circuitry of the medical device system, a plurality of evaluations, wherein, for each of the evaluations, the method comprises:
determining that the evaluation is prompted, wherein the evaluation is associated with a current measurement of the tissue oxygen saturation parameter;
controlling the optical sensor to perform an ambient light measurement associated with the current measurement of the tissue oxygen saturation parameter;
based on the ambient light measurement, performing at least one of:
determining whether to control the optical sensor to perform the current measurement of the tissue oxygen saturation parameter,
determining when to control the optical sensor to perform the current measurement of the tissue oxygen saturation parameter, or
determining whether to include the current measurement of the tissue oxygen saturation parameter in a trend of the tissue oxygen saturation parameter; and
completing the evaluation based on determining at least one of whether to control the optical sensor to perform the current measurement, when to control the optical sensor to perform the current measurement, or whether to include the current measurement in the trend.

20. A non-transitory computer-readable medium storing instructions for causing processing circuitry to perform a method comprising:
measuring, using an optical sensor, ambient light and a tissue oxygen saturation parameter;
performing, using processing circuitry of the medical device system, a plurality of evaluations, wherein, for each of the evaluations, the method comprises:
determining that the evaluation is prompted, wherein the evaluation is associated with a current measurement of the tissue oxygen saturation parameter;
controlling the optical sensor to perform an ambient light measurement associated with the current measurement of the tissue oxygen saturation parameter;
based on the ambient light measurement, performing at least one of:
determining whether to control the optical sensor to perform the current measurement of the tissue oxygen saturation parameter,
determining when to control the optical sensor to perform the current measurement of the tissue oxygen saturation parameter, or
determining whether to include the current measurement of the tissue oxygen saturation parameter in a trend of the tissue oxygen saturation parameter; and
completing the evaluation based on determining at least one of whether to control the optical sensor to perform the current measurement, when to control the optical sensor to perform the current measurement, or whether to include the current measurement in the trend.

* * * * *